(12) United States Patent
Møller

(10) Patent No.: US 8,951,984 B2
(45) Date of Patent: Feb. 10, 2015

(54) OLIGONUCLEOTIDES FOR MODULATION OF TARGET RNA ACTIVITY

(71) Applicant: MirrX Therapeutics A/S, Kongens, Lyngby (DK)

(72) Inventor: Thorleif Møller, Arslev (DK)

(73) Assignee: MirrX Therapeutics A/S, Vejle (DK)

( * ) Notice: Subject to any disclaimer, the term of this patent is extended or adjusted under 35 U.S.C. 154(b) by 0 days.

(21) Appl. No.: 14/246,997

(22) Filed: Apr. 7, 2014

(65) Prior Publication Data

US 2014/0249206 A1  Sep. 4, 2014

Related U.S. Application Data

(62) Division of application No. 12/664,502, filed as application No. PCT/DK2008/050141 on Jun. 13, 2008, now Pat. No. 8,691,965.

(30) Foreign Application Priority Data

| Jun. 14, 2007 | (DK) | 2007 00860 |
| Oct. 16, 2007 | (DK) | 2007 01493 |
| Oct. 18, 2007 | (DK) | 2007 01504 |
| Nov. 9, 2007 | (DK) | 2007 01580 |
| Dec. 3, 2007 | (DK) | 2007 01725 |
| Feb. 15, 2008 | (DK) | 2008 00214 |

(51) Int. Cl.

| A61K 31/70 | (2006.01) |
| C07H 21/02 | (2006.01) |
| C07H 21/04 | (2006.01) |
| C12N 15/113 | (2010.01) |
| C12Q 1/68 | (2006.01) |

(52) U.S. Cl.
CPC ...... *C12N 15/1131* (2013.01); *C12N 2310/141* (2013.01); *C12N 15/113* (2013.01); *C12N 2310/113* (2013.01)
USPC ......... 514/44 A; 435/375; 435/377; 536/23.1; 536/24.1; 536/24.5

(58) Field of Classification Search
None
See application file for complete search history.

(56) References Cited

U.S. PATENT DOCUMENTS

| 6,284,458 | B1 | 9/2001 | Anderson et al. |
| 6,391,542 | B1 | 5/2002 | Anderson et al. |
| 6,423,489 | B1 | 7/2002 | Anderson et al. |
| 6,433,159 | B1 | 8/2002 | Anderson |
| 6,617,438 | B1 | 9/2003 | Beigelman et al. |
| 8,084,433 | B2 | 12/2011 | Iversen et al. |
| 8,129,352 | B2 | 3/2012 | Iversen et al. |
| 8,288,356 | B2 * | 10/2012 | Obad et al. ......... 514/44 A |
| 2005/0227934 | A1 | 10/2005 | Stoffel et al. |

FOREIGN PATENT DOCUMENTS

| WO | WO 94/05813 | 3/1994 |
| WO | WO 2004/005543 A1 | 1/2004 |
| WO | WO 2004/048511 A2 | 6/2004 |
| WO | WO 2008/061537 A2 | 5/2008 |
| WO | WO 2008/074328 A2 | 6/2008 |

OTHER PUBLICATIONS

International Search Report PCT/DK2008/050141 dated Jun. 2, 2009.
Database EMBL [Online] Apr. 19, 2007, "Wang-VSVgfp-Jurkat-454-Avr-122495_1064_3 813 Wang-VSVGgfp-Jurkat-454-Avr *Homo sapiens* genomic, genomic survey sequence", XP002522086 retrieved from EBI accession No. EMBL:EI561734 Database accession No. EI561734.
Jiening Xiao et al., "Novel Approaches for Gene-Specific Interference Via Manipulating Actions of MicroRNAs: Examination on the Pacemaker Channel Genes HCN2 and HCN4", Journal of Cellular Physiology, May 21, 2007 pp. 285-292.
Catherine L. Jopling et al., "Modulation of Hepatitis C Virus RNA Abundance by a Liver-Specific MicroRNA", Science, 309, pp. 1577-1581 (2005).

\* cited by examiner

*Primary Examiner* — Sean McGarry
(74) *Attorney, Agent, or Firm* — Foley & Lardner LLP

(57) ABSTRACT

The present invention relates to oligonucleotides for modulation of target RNA activity. Thus, the invention provides oligonucleotides that bind to microRNA binding sites of target RNA. The oligonucleotides may activate RNase H or RNAi. In a preferred embodiment, the oligonucleotides prevents a microRNA from binding to its binding site of the target RNA and thereby prevent the microRNA from regulating the target RNA. Such oligonucleotides have uses in research and development of new therapeutics.

14 Claims, No Drawings

SEQUENCE LISTING

```
<160> NUMBER OF SEQ ID NOS: 56

<210> SEQ ID NO 1
<211> LENGTH: 40
<212> TYPE: RNA
<213> ORGANISM: Homo Sapiens

<400> SEQUENCE: 1
guuuuaaguu uuguguugca agaacaaaug gaauaaacuu                         40

<210> SEQ ID NO 2
<211> LENGTH: 40
<212> TYPE: RNA
<213> ORGANISM: Homo Sapiens

<400> SEQUENCE: 2
ccgccccgcc ccggcaggcc cggccccacc ccgccccgcc                         40

<210> SEQ ID NO 3
<211> LENGTH: 40
<212> TYPE: RNA
<213> ORGANISM: Homo Sapiens

<400> SEQUENCE: 3
gccagccccc ugauggggc gacacuccac cauagaucac                          40

<210> SEQ ID NO 4
<211> LENGTH: 40
<212> TYPE: RNA
<213> ORGANISM: Homo Sapiens
```

<400> SEQUENCE: 4
uauuuauauu cagaaaagaa acauuucagu aauuuauaau                              40

<210> SEQ ID NO 5
<211> LENGTH: 40
<212> TYPE: RNA
<213> ORGANISM: Homo Sapiens

<400> SEQUENCE: 5
cauaauccuu ggaaaacuua aguucucauu caccccaguu                              40

<210> SEQ ID NO 6
<211> LENGTH: 40
<212> TYPE: RNA
<213> ORGANISM: Homo Sapiens

<400> SEQUENCE: 6
cccccaaauc cggaagucaa aguucucaug gucagaaguu                              40

<210> SEQ ID NO 7
<211> LENGTH: 40
<212> TYPE: RNA
<213> ORGANISM: Homo Sapiens

<400> SEQUENCE: 7
ucugccucua aaagcguugg auguagcauu augcaauuag                              40

<210> SEQ ID NO 8
<211> LENGTH: 40
<212> TYPE: RNA
<213> ORGANISM: Homo Sapiens

<400> SEQUENCE: 8
guauauaguu uuuaccuuuu auguagcaca uaaacuuugg                              40

<210> SEQ ID NO 9
<211> LENGTH: 40
<212> TYPE: RNA
<213> ORGANISM: Homo Sapiens

<400> SEQUENCE: 9
aaaguuuguu agauagcugc auguggcuuu uuuaaaaaag                              40

<210> SEQ ID NO 10
<211> LENGTH: 40
<212> TYPE: RNA
<213> ORGANISM: Homo Sapiens

<400> SEQUENCE: 10
ucuagacaau auacaagcca aaguggcaug uuuugugcau                              40

<210> SEQ ID NO 11
<211> LENGTH: 40
<212> TYPE: RNA
<213> ORGANISM: Homo Sapiens
<220> FEATURE:
<221> NAME/KEY: misc_feature
<222> LOCATION: (36)..(40)
<223> OTHER INFORMATION: n is a, c, g, or u

<400> SEQUENCE: 11
cagugucaaa uaaacacugu guaagcuaaa aaaannnnn                               40

```
<210> SEQ ID NO 12
<211> LENGTH: 40
<212> TYPE: RNA
<213> ORGANISM: Homo Sapiens

<400> SEQUENCE: 12
auuuaguaca guuuagaaag agcacuuauu uuguuuauau                                40

<210> SEQ ID NO 13
<211> LENGTH: 40
<212> TYPE: RNA
<213> ORGANISM: Homo Sapiens

<400> SEQUENCE: 13
uacauuugua uuuuauccau agcacuuauu cacauuuagg                                40

<210> SEQ ID NO 14
<211> LENGTH: 40
<212> TYPE: RNA
<213> ORGANISM: Homo Sapiens

<400> SEQUENCE: 14
uaacacagua uaucccaagu gcacuuucua auguuucugg                                40

<210> SEQ ID NO 15
<211> LENGTH: 40
<212> TYPE: RNA
<213> ORGANISM: Homo Sapiens

<400> SEQUENCE: 15
uacaauagcc aauaacauuu gcacuuuauu aaugccugua                                40

<210> SEQ ID NO 16
<211> LENGTH: 40
<212> TYPE: RNA
<213> ORGANISM: Homo Sapiens

<400> SEQUENCE: 16
gagcagcauu uauagaguuu gauggcaaau agauuaggca                                40

<210> SEQ ID NO 17
<211> LENGTH: 40
<212> TYPE: RNA
<213> ORGANISM: Homo Sapiens

<400> SEQUENCE: 17
uggcaacaga uaaguuugca guuggcuaag agagguuucc                                40

<210> SEQ ID NO 18
<211> LENGTH: 40
<212> TYPE: RNA
<213> ORGANISM: Homo Sapiens

<400> SEQUENCE: 18
ugugcagcag cuuacauguc ugaaguuacu ugaaggcauc                                40

<210> SEQ ID NO 19
<211> LENGTH: 40
<212> TYPE: RNA
<213> ORGANISM: Homo Sapiens

<400> SEQUENCE: 19
guucacuagc uguggucuga ccuaguuaau uuacaaauac                                40
```

```
<210> SEQ ID NO 20
<211> LENGTH: 40
<212> TYPE: RNA
<213> ORGANISM: Homo Sapiens

<400> SEQUENCE: 20
auaggacauu gugucagauu accaguuaua ggaacaauuc                              40

<210> SEQ ID NO 21
<211> LENGTH: 40
<212> TYPE: RNA
<213> ORGANISM: Homo Sapiens

<400> SEQUENCE: 21
ggauugugga acuucuggga cgcaggggu gggaagcccu                               40

<210> SEQ ID NO 22
<211> LENGTH: 40
<212> TYPE: RNA
<213> ORGANISM: Homo Sapiens

<400> SEQUENCE: 22
gaacuucugg gacgcagggg gugggaagcc cucaaauauu                              40

<210> SEQ ID NO 23
<211> LENGTH: 40
<212> TYPE: RNA
<213> ORGANISM: Homo Sapiens

<400> SEQUENCE: 23
agggccaggg gucagauauc cacugaccuu uggauggugc                              40

<210> SEQ ID NO 24
<211> LENGTH: 40
<212> TYPE: RNA
<213> ORGANISM: Homo Sapiens

<400> SEQUENCE: 24
gacaucgagc uugcuacaag ggacuuuccg cugggacuu                               40

<210> SEQ ID NO 25
<211> LENGTH: 40
<212> TYPE: RNA
<213> ORGANISM: Homo Sapiens

<400> SEQUENCE: 25
agaccagauc ugagccuggg agcucucugg cuaacuaggg                              40

<210> SEQ ID NO 26
<211> LENGTH: 40
<212> TYPE: RNA
<213> ORGANISM: Homo Sapiens

<400> SEQUENCE: 26
caauacauuu gaaaacuugu uugggagacu cugcauuuuu                              40

<210> SEQ ID NO 27
<211> LENGTH: 40
<212> TYPE: RNA
<213> ORGANISM: Homo Sapiens

<400> SEQUENCE: 27
```

```
gcaugcguug cacuucuuuu uugggagaug uguguuguug                              40

<210> SEQ ID NO 28
<211> LENGTH: 40
<212> TYPE: RNA
<213> ORGANISM: Homo Sapiens

<400> SEQUENCE: 28
caacaugaaa cuuuucauga augggagaag aaccuauuuu                              40

<210> SEQ ID NO 29
<211> LENGTH: 40
<212> TYPE: RNA
<213> ORGANISM: Homo Sapiens

<400> SEQUENCE: 29
uagccugacu guuuuauaau uugggaguuc ugcauuugau                              40

<210> SEQ ID NO 30
<211> LENGTH: 40
<212> TYPE: RNA
<213> ORGANISM: Homo Sapiens

<400> SEQUENCE: 30
auuauuuuuu caucguaaug caggguaacu auuauugcgc                              40

<210> SEQ ID NO 31
<211> LENGTH: 40
<212> TYPE: RNA
<213> ORGANISM: Homo Sapiens

<400> SEQUENCE: 31
acucccugcc uggaucucac cagcacuuuc ccucuguuuc                              40

<210> SEQ ID NO 32
<211> LENGTH: 40
<212> TYPE: RNA
<213> ORGANISM: Homo Sapiens

<400> SEQUENCE: 32
auucccugcc uggaucucac gagcacuuuc ccucuggug                               40

<210> SEQ ID NO 33
<211> LENGTH: 40
<212> TYPE: RNA
<213> ORGANISM: Homo Sapiens

<400> SEQUENCE: 33
cuucuuaagu ggaauauucu aauaagcuac cuuuuguaag                              40

<210> SEQ ID NO 34
<211> LENGTH: 40
<212> TYPE: RNA
<213> ORGANISM: Homo Sapiens

<400> SEQUENCE: 34
auguuugcac uugugauuau uuauuauuua uuuauuauuu                              40

<210> SEQ ID NO 35
<211> LENGTH: 40
<212> TYPE: RNA
<213> ORGANISM: Homo Sapiens

<400> SEQUENCE: 35
```

```
ugugauuauu uauuauuuau uuauuauuua uuuauuuaca                    40

<210> SEQ ID NO 36
<211> LENGTH: 40
<212> TYPE: RNA
<213> ORGANISM: Homo Sapiens

<400> SEQUENCE: 36
uuuacagaug aauguauuua uuugggagac cggggguaucc                   40

<210> SEQ ID NO 37
<211> LENGTH: 40
<212> TYPE: RNA
<213> ORGANISM: Homo Sapiens

<400> SEQUENCE: 37
ggguauccug ggggacccaa uguaggagcu gccuuuuuc                     40

<210> SEQ ID NO 38
<211> LENGTH: 40
<212> TYPE: RNA
<213> ORGANISM: Homo Sapiens

<400> SEQUENCE: 38
gcucaaaaag agaauugggg gcuuagggug ggaacccaag                    40

<210> SEQ ID NO 39
<211> LENGTH: 40
<212> TYPE: RNA
<213> ORGANISM: Homo Sapiens

<400> SEQUENCE: 39
cuagaaauug acacaagugg accuuaggcc uuccucucuc                    40

<210> SEQ ID NO 40
<211> LENGTH: 40
<212> TYPE: RNA
<213> ORGANISM: Homo Sapiens

<400> SEQUENCE: 40
cugacaucug gaaucuggag accagggagc cuuugguucu                    40

<210> SEQ ID NO 41
<211> LENGTH: 40
<212> TYPE: RNA
<213> ORGANISM: Homo Sapiens

<400> SEQUENCE: 41
cauugcugag ccucugcucc ccaggggagu ugugucugua                    40

<210> SEQ ID NO 42
<211> LENGTH: 40
<212> TYPE: RNA
<213> ORGANISM: Homo Sapiens

<400> SEQUENCE: 42
aaccugggau ucaggaaugu guggccugca cagugaagug                    40

<210> SEQ ID NO 43
<211> LENGTH: 40
<212> TYPE: RNA
<213> ORGANISM: Homo Sapiens
```

<400> SEQUENCE: 43
aggcuguucc cauguagccc ccuggccucu gugccuucuu          40

<210> SEQ ID NO 44
<211> LENGTH: 40
<212> TYPE: RNA
<213> ORGANISM: Homo Sapiens

<400> SEQUENCE: 44
ugccuggguc ccuguuacaa gucaggagcc cuguagggag          40

<210> SEQ ID NO 45
<211> LENGTH: 40
<212> TYPE: RNA
<213> ORGANISM: Homo Sapiens

<400> SEQUENCE: 45
agcacagcag ggcauauacc agucaggaau gcccguuacc          40

<210> SEQ ID NO 46
<211> LENGTH: 40
<212> TYPE: RNA
<213> ORGANISM: Homo Sapiens

<400> SEQUENCE: 46
guugagagag ugcaggcugg ggucaggaca ggcugcggau          40

<210> SEQ ID NO 47
<211> LENGTH: 40
<212> TYPE: RNA
<213> ORGANISM: Homo Sapiens

<400> SEQUENCE: 47
uauguauauu gcugaguuga aagcacuuau uggaaaauau          40

<210> SEQ ID NO 48
<211> LENGTH: 40
<212> TYPE: RNA
<213> ORGANISM: Homo Sapiens

<400> SEQUENCE: 48
ccagagaugg uuuuccacuc cuucuagaua uucccaaaaa          40

<210> SEQ ID NO 49
<211> LENGTH: 40
<212> TYPE: RNA
<213> ORGANISM: Homo Sapiens

<400> SEQUENCE: 49
uacacaucuu caacagaccc ccucuagaaa uuuuucagau          40

<210> SEQ ID NO 50
<211> LENGTH: 40
<212> TYPE: RNA
<213> ORGANISM: Homo Sapiens

<400> SEQUENCE: 50
gacuuuucag agcacacccu uccucugguu uuuguauauu          40

<210> SEQ ID NO 51
<211> LENGTH: 40
<212> TYPE: RNA
<213> ORGANISM: Homo Sapiens

```
<400> SEQUENCE: 51
acuaguuuuc aaucauaaua ccugcugugg augcuucaug                           40

<210> SEQ ID NO 52
<211> LENGTH: 40
<212> TYPE: RNA
<213> ORGANISM: Homo Sapiens

<400> SEQUENCE: 52
ggaauuggcc gcugucacug cuuguuguuu gcgcauuuuu                           40

<210> SEQ ID NO 53
<211> LENGTH: 40
<212> TYPE: RNA
<213> ORGANISM: Homo Sapiens

<400> SEQUENCE: 53
agauguccau uuguuauugu guuuguuaac aacccuuuau                           40

<210> SEQ ID NO 54
<211> LENGTH: 40
<212> TYPE: RNA
<213> ORGANISM: Homo Sapiens

<400> SEQUENCE: 54
gcuggauagu aguuauguug cugugaaaac uguaggguca                           40

<210> SEQ ID NO 55
<211> LENGTH: 40
<212> TYPE: RNA
<213> ORGANISM: Homo Sapiens

<400> SEQUENCE: 55
aaugugugga aucacaaguu gcugugauac uucauuuuua                           40

<210> SEQ ID NO 56
<211> LENGTH: 40
<212> TYPE: RNA
<213> ORGANISM: Homo Sapiens

<400> SEQUENCE: 56
cugaccuuuc auauggauua uugugaguca ucagaguuua                           40
```

OLIGONUCLEOTIDES FOR MODULATION OF TARGET RNA ACTIVITY

CROSS-REFERENCE TO RELATED APPLICATION(S)

This application is a divisional of U.S. patent application Ser. No. 12/664,502, filed Jun. 13, 2008, which is the National Phase of International Patent Application No. PCT/DK2008/050141, filed Jun. 13, 2008, which claims priority from Denmark Patent Application Nos. PA200700860, filed Jun. 14, 2007, PA200701493, filed Oct. 16, 2007, PA200701504, filed Oct. 18, 2007, PA200701580, filed Nov. 9, 2007, PA200701725, filed Dec. 3, 2007, and PA200800214, filed Feb. 15, 2008. The contents of these applications are herein incorporated by reference in their entirety.

BACKGROUND OF THE INVENTION

The present invention relates to oligonucleotides that can be used to affect the activity of target RNAs.

The first generation of such oligonucleotides were antisense oligonucleotides that were intended to affect the activity of target mRNAs. One reason for interest in such oligonucleotides is the potential for exquisite and predictable specificity that can be achieved because of specific base pairing. In other words, it is in theory very simple to design an oligonucleotide that is highly specific for a given nucleic acid, such as an mRNA.

However, it has turned out simple base pairing is not enough to achieve regulation of a given target mRNA, i.e. an oligonucleotide complementary to a given target mRNA does not necessarily affect the activity of the target mRNA. If the oligonucleotide targets the open reading frame of an mRNA, it may e.g. be that the translational apparatus simply displaces the oligonucleotide during translation. Therefore, means where developed that would improve the regulatory activity of the oligonucleotide.

E.g. oligonucleotides that can activate RNase H cleavage of the target mRNA were developed. One potential disadvantage of such oligonucleotides is that they may mediate cleavage of other RNAs than the intended target mRNA, i.e. giving rise to off-target effects. Still, such oligonucleotides acting through RNase H cleavage are in clinical trials for treatment of various diseases.

Recently, research has shown that eukaryotic cells, including mammalian cells, comprise a complex gene regulatory system (herein also termed RNAi machinery) that uses RNA as specificity determinants. This system can be triggered by so called siRNAs that may be introduced into a cell of interest to regulate the activity of a target mRNA. Currently, massive efforts go into triggering the RNAi machinery with siRNAs for specific regulation of target RNAs, in particular target mRNAs. This approach is widely regarded as having great promise for the development of new therapeutics. As will also be outlined below, a major advantage of this approach is that specificity of the siRNA lies in the degree of complementarity between the guide strand of the siRNA and the target RNA, i.e. target specificity can be controlled. However, it has turned out that siRNAs may be less specific than initially thought. Initially, it was believed that only target RNAs that harboured stretches of complete complementarity to the guide strand of the siRNA would be affected, i.e. targeted by the RNAi machinery. New research indicates that siRNAs indeed do result in significant off-target effects, i.e. regulation of non-intended targets. It is now believed that these off-targets stem from the siRNAs, or rather the guide strand of the siRNAs, acting as microRNAs.

MicroRNAs are a class of endogenous RNA molecules that has recently been discovered and that, as siRNA, function via the RNAi machinery. Currently, about 500 human microRNAs have been discovered and the number is rapidly increasing. It is now believed that more than one third of all human genes may be regulated by microRNAs. Therefore, microRNAs themselves may be used to regulate the activity of target RNAs, and consequently e.g. be used as therapeutics.

However, microRNAs generally act at more than one target RNA, i.e. they are promiscuous. Thus, introduction of a microRNA into the cell or regulating the level of a microRNA will affect the activity of more than one target mRNA and consequently often give rise to undesired off-target effects.

A recent approach has been put forward, wherein the activity of a target RNA is regulated by inhibiting the activity of a microRNA. The microRNA can be inhibited using complementary oligonucleotides that have been termed antimirs and antagomirs. Since the microRNA is itself promiscuous, also an antimir or antagomir will be promiscuous and affect the activity of more than one target RNA.

SUMMARY OF THE INVENTION

The present invention relates to oligonucleotides for modulating the activity of a target RNA. The oligonucleotides of the invention may activate RNaseH, RNAi or prevent RNAi. In a preferred embodiment, oligonucleotides of the invention are capable of preventing a microRNA from regulating a target RNA.

Thus, a first aspect of the invention is an oligonucleotide comprising a contiguous sequence complementary to at least 8 contiguous bases of any of SEQ ID NO:1-56 or any of SEQ ID NO:1-56 comprising 1, 2 or 3 substitutions.

Other aspects of the invention relates to a method of modulating the activity of a target RNA, a pharmaceutical composition comprising an effective amount of the oligonucleotide of the invention, the oligonucleotide of the invention for use as medicine and a method of treatment comprising administering a therapeutically effective amount of the oligonucleotide of the invention to a person in need thereof.

DETAILED DESCRIPTION OF THE INVENTION

Definitions

In previous application, PA 2007 00860, Xmirs from microRNA targets, the term Xmir was used, when referring to oligonucleotides of the invention. In this application, the term oligonucleotide of the invention or alternatively blockmir is preferentially used over the term Xmir. Thus, when the term Xmir or blockmir is used, reference is to oligonucleotides of the invention. A blockmir is a particular preferred embodiment of the oligonucleotides of the invention, wherein the oligonucleotide can be used to prevent microRNA regulation of a specific target RNA. The terms "regulate" and "modulate" are used interchangeably herein.

When referring to the "activity of a target mRNA", what is typically meant is the expression of the target mRNA, i.e. translation into a protein or peptide. Thus, regulation of the activity of a target mRNA may include degradation of the mRNA and/or translational regulation. Regulation may also include affecting intracellular transport of the mRNA. In a preferred embodiment of the invention, the oligonucleotide is capable of regulating the expression of the target mRNA. In another preferred embodiment, the oligonucleotide may mediate degradation of the target mRNA. The activity may also be replication.

When the target RNA is a viral RNA, the oligonucleotide of the invention may affect replication of the virus or otherwise interfere with the proliferation of the virus.

As used herein, regulation may be either positive or negative. I.e. a regulator (e.g. oligonucleotide or microRNA) may increase the activity of the target (e.g. target mRNA) or it may decrease the activity of the target.

When referring to the "target sequence of an RNA", what is meant is the region of the RNA involved in or necessary for microRNA regulation. The terms target region and target sequence are used interchangeably herein. Not intended to be bound by theory, it is believed that this region comprise bases that interact directly with the microRNA during microRNA regulation of the target RNA. In a preferred embodiment, the target sequence is the region of the target RNA necessary for microRNA regulation. Such region may be defined using a reporter system, wherein systematic deletions of the target RNA are tested for activity to define the target sequence. As will be clear from the specification, also oligonucleotides of the invention may be used to define the region of the target RNA necessary for microRNA regulation. Preferably, the target sequence comprises an antiseed sequence, which is complementary to the seed sequence of a microRNA and also complementary to a guide sequence of a oligonucleotide of the invention.

The term microRNA as used herein has the same meaning as typically in the art. I.e. the term microRNA refers to a small non-translated RNA of typically 18-22 nucleotides that is capable of regulating the activity of a target mRNA. A microRNA is typically processed from pri-microRNA to short stem-loop structures called pre-microRNA and finally to mature miRNA. Both strands of the stem of the pre-microRNA may be processed to a mature microRNA.

The miRBase (http://microrna.sanger.ac.uk/sequences/) is a compilation of known microRNAs. Also predicted and known targets of the microRNAs can be found on this site.

The term siRNA (short interfering RNA) as used herein has the same meaning as typically in the art. I.e. the term siRNA refers to double stranded RNA complex wherein the strands are typically 18-22 nucleotides in length. Very often, the complex has 3'-overhangs.

When referring to the RNAi machinery herein, what is meant are the cellular components necessary for the activity of siRNAs and microRNAs or for the RNAi pathway. A major player of the RNAi machinery is the RNA induced silencing complex (the RISC complex).

As referred to herein, an RNA unit is one of the monomers that make up an RNA polymer. Thus, an RNA unit is also referred to as an RNA monomer or a RNA nucleotide. Likewise, a DNA unit is one of the monomers that make up a DNA polymer and a DNA unit may also be referred to as a DNA monomer or a DNA nucleotide.

When referring to a base, what is meant is the base of a nucleotide. The base may be part of DNA, RNA, INA, LNA or any other nucleic acid or nucleic acid capable of specific base pairing. The base may also be part of PNA (peptide nucleic acid) or morpholino. In some embodiments, the base may be a universal base.

When referring the length of a sequence, reference may be made to the number of units or to the number of bases.

When referring to a complementary sequence, G pairs to C, A pairs to T and U and vice versa. In a preferred embodiment, G also pairs to U and vice versa to form a so-called wobble base pair. In another preferred embodiment, the base inosine (I) may be comprised within either in a microRNA or oligonucleotide of the invention. I base pairs to A, C and U. In still another preferred embodiment, universal bases may be used. Universal bases can typically basepair to G, C, A, U and T. Often universal bases do not form hydrogen bonds with the opposing base on the other strand. In still another preferred embodiment, a complementary sequence refers to a contiguous sequence exclusively of Watson-Crick base pairs.

As used herein, the term "capable of base pairing with" is used interchangeably with "complementary to". Thus, in one embodiment, the oligonucleotide comprises one or more inosine bases.

First Aspect

In a first aspect, the present invention provides an oligonucleotide comprising a contiguous sequence complementary to at least 8 contiguous bases of any of SEQ ID NOs:1-56 or any of SEQ ID NOs:1-56 comprising 1, 2 or 3 substitutions.

When referring to a substitution herein, it means that the base at a particular position may have been substituted for another base. The substitution may be because of the presence of a single nucleotide polymorphism in the target RNA. In one embodiment, the term substitution also covers deletions and additions. More preferably, the term substitution does not cover deletions and additions.

SEQ ID NOs:1-56 represents sequences of verified microRNA targets (also termed target RNAs) or putative microRNA targets. Therefore, oligonucleotides of the invention can be used to verify whether SEQ ID NOs: 1-56 do indeed comprise a microRNA target and is subject to microRNA regulation. Moreover, the oligonucleotides of the invention may also be used to modulate the activity of the target RNA, e.g. to study regulatory networks in basic research.

The oligonucleotides of the invention may also find therapeutic application, e.g. when a particular microRNA is upregulated and cause unwanted microRNA regulation of a target RNA. Another situation is when the presence of a SNP (single nucleotide polymorphism) gives rise to a microRNA target and hence cause unwanted microRNA regulation. Examples are further given in the examples section.

TABLE 1

List of target sequences.

| SEQ ID NO | GENE | SEQUENCE |
|---|---|---|
| 1 | Mtpn | GUUUUAAGUUUUGUGUUGCAAGAACAAAUGGAAUAAACUU |
| 2 | TGFB1 | CCGCCCCGCCCCGGCAGGCCCGGCCCCACCCCGCCCCGCC |
| 3 | 5'UTR | GCCAGCCCCCUGAUGGGGCGACACUCCACCAUAGAUCAC |
| 4 | SOCS-3 | UAUUUAUAUUCAGAAAAGAAACAUUUCAGUAAUUUAUAAU |

TABLE 1-continued

List of target sequences.

| SEQ ID NO | GENE | SEQUENCE |
|---|---|---|
| 5 | Traf-6 | CAUAAUCCUUGGAAAACUUAAGUUCUCAUUCACCCCAGUU |
| 6 | Irak-I | CCCCCAAAUCCGGAAGUCAAAGUUCUCAUGGUCAGAAGUU |
| 7 | P27kip1 | UCUGCCUCUAAAAGCGUUGGAUGUAGCAUUAUGCAAUUAG |
| 8 | P27kip1 | GUAUAUAGUUUUUACCUUUUAUGUAGCACAUAAACUUUGG |
| 9 | P27kip1 | AAAGUUUGUUAGAUAGCUGCAUGUGGCUUUUUUAAAAAG |
| 10 | P27kip1 | UCUAGACAAUAUACAAGCCAAAGUGGCAUGUUUUGUGCAU |
| 11 | TPM1 | CAGUGUCAAAUAAACACUGUGUAAGCUAAAAAAAANNNNN |
| 12 | LATS2 | AUUUAGUACAGUUUAGAAAGAGCACUUAUUUUGUUUAUAU |
| 13 | LATS2 | UACAUUUGUAUUUUAUCCAUAGCACUUAUUCACAUUUAGG |
| 14 | RB1 | UAACACAGUAUAUCCCAAGUGCACUUUCUAAUGUUUCUGG |
| 15 | TGFBR2 | UACAAUAGCCAAUAACAUUUGCACUUUAUUAAUGCCUGUA |
| 16 | PTEN | GAGCAGCAUUUAUAGAGUUUGAUGGCAAAUAGAUUAGGCA |
| 17 | PTEN | UGGCAACAGAUAAGUUUGCAGUUGGCUAAGAGAGGUUUCC |
| 18 | PTEN | UGUGCAGCAGCUUACAUGUCUGAAGUUACUUGAAGGCAUC |
| 19 | PTEN | GUUCACUAGCUGUGGUCUGACCUAGUUAAUUUACAAAUAC |
| 20 | PTEN | AUAGGACAUUGUGUCAGAUUACCAGUUAUAGGAACAAUUC |
| 21 | HIV3'UTR | GGAUUGUGGAACUUCUGGGACGCAGGGGGUGGGAAGCCCU |
| 22 | HIV3'UTR | GAACUUCUGGGACGCAGGGGGUGGGAAGCCCUCAAAUAUU |
| 23 | HIV3'UTR | AGGGCCAGGGGUCAGAUAUCCACUGACCUUUGGAUGGUGC |
| 24 | HIV3'UTR | GACAUCGAGCUUGCUACAAGGGACUUUCCGCUGGGGACUU |
| 25 | HIV3'UTR | AGACCAGAUCUGAGCCUGGGAGCUCUCUGGCUAACUAGGG |
| 26 | c-myb | CAAUACAUUUGAAAACUUGUUUGGGAGACUCUGCAUUUUU |
| 27 | c-myb | GCAUGCGUUGCACUUCUUUUUUGGGAGAUGUGUGUUGUUG |
| 28 | c-myb | CAACAUGAAACUUUUCAUGAAUGGGAGAAGAACCUAUUUU |
| 29 | c-myb | UAGCCUGACUGUUUUAUAAUUUGGGAGUUCUGCAUUUGAU |
| 30 | HOXD10 | AUUAUUUUUUCAUCGUAAUGCAGGGUAACUAUUAUUGCGC |
| 31 | micb | ACUCCCUGCCUGGAUCUCACCAGCACUUUCCCUCUGUUUC |
| 32 | mica | AUUCCCUGCCUGGAUCUCACGAGCACUUUCCCUCUUGGUG |
| 33 | Pdcd4 | CUUCUUAAGUGGAAUAUUCUAAUAAGCUACCUUUUGUAAG |
| 34 | tnf | AUGUUUGCACUUGUGAUUAUUUAUUAUUUAUUUAUUAUUU |
| 35 | tnf | UGUGAUUAUUUAUUAUUUAUUUAUUAUU**UAUUUAUUUACA |
| 36 | tnf | UUUACAGAUGAAUGUAUUUAUUUGGGAGACCGGGGUAUCC |
| 37 | tnf | GGGUAUCCUGGGGGACCCAAUGUAGGAGCUGCCUUUUUUC |
| 38 | tnf | GCUCAAAAAGAGAAUUGGGGGCUUAGGGUCGGAACCCAAG |
| 39 | tnf | CUAGAAAUUGACACAAGUGGACCUUAGGCCUUCCUCUCUC |
| 40 | tnf | CUGACAUCUGGAAUCUGGAGACCAGGGAGCCUUUGGUUCU |
| 41 | tnf | CAUUGCUGAGCCUCUGCUCCCCAGGGGAGUUGUGUCUGUA |
| 42 | tnf | AACCUGGGAUUCAGGAAUGUGUGGCCUGCACAGUGAAGUG |

TABLE 1-continued

List of target sequences.

| SEQ ID NO | GENE | SEQUENCE |
|---|---|---|
| 43 | tnf | AGGCUGUUCCCAUGUAGCCCCCUGGCCUCUGUGCCUUCUU |
| 44 | sufu | UGCCUGGGUCCCUGUUACAAGUCAGGAGCCCUGUAGGGAG |
| 45 | Fus-1 | AGCACAGCAGGGCAUAUACCAGUCAGGAAUGCCCGUUACC |
| 46 | Fus-1 | GUUGAGAGAGUGCAGGCUGGGGUCAGGACAGGCUGCGGAU |
| 47 | cd44 | UAUGUAUAUUGCUGAGUUGAAAGCACUUAUUGGAAAAUAU |
| 48 | cd44 | CCAGAGAUGGUUUUCCACUCCUUCUAGAUAUUCCCAAAAA |
| 49 | cd44 | UACACAUCUUCAACAGACCCCCUCUAGAAAUUUUUCAGAU |
| 50 | cd44 | GACUUUUCAGAGCACACCCUUCCUCUGGUUUUUGUAUAUU |
| 51 | pten | ACUAGUUUUCAAUCAUAAUACCUGCUGUGGAUGCUUCAUG |
| 52 | pten | GGAAUUGGCCGCUGUCACUGCUUGUUGUUUGCGCAUUUUU |
| 53 | pten | AGAUGUCCAUUUGUUAUUGUGUUUGUUAACAACCCUUUAU |
| 54 | ZBTB10 | GCUGGAUAGUAGUUAUGUUGCUGUGAAAACUGUAGGGUCA |
| 55 | Myt1I | AAUGUGUGGAAUCACAAGUUGCUGUGAUACUUCAUUUUUA |
| 56 | Myt1I | CUGACCUUUCAUAUGGAUUAUUGUGAGUCAUCAGAGUUUA |

Contiguous Complementary Sequences

In another embodiment, the oligonucleotide of the invention comprises a contiguous sequence complementary to a sequence selected from the group consisting of at least 9 contiguous bases, at least 10 contiguous bases, at least 11 contiguous bases, at least 12 contiguous bases, at least 13 contiguous bases, at least 14 contiguous bases, at least 15 contiguous bases, at least 16 contiguous bases, at least 17 contiguous bases, at least 18 contiguous bases, at least 19 contiguous bases, at least 20 contiguous bases, at least 22 contiguous bases, at least 25 contiguous bases, at least 30 contiguous bases, and at least 35 contiguous bases of any of SEQ ID NO:1-56 or any of SEQ ID NO:1-56 comprising 1, 2 or 3 substitutions.

In yet another embodiment, the oligonucleotide of the invention comprises a contiguous sequence complementary to a sequence selected from the group consisting of no more than 8 contiguous bases, no more than 9 contiguous bases, no more than 10 contiguous bases, no more than 11 contiguous bases, no more than 12 contiguous bases, no more than 13 contiguous bases, no more than 14 contiguous bases, no more than 15 contiguous bases, no more than 16 contiguous bases, no more than 17 contiguous bases, no more than 18 contiguous bases, no more than 19 contiguous bases, no more than 20 contiguous bases, no more than 22 contiguous bases, no more than 25 contiguous bases, no more than 30 contiguous bases, and no more than 35 contiguous bases of any of SEQ ID NO:1-56 or any of SEQ ID NO:1-56 comprising 1, 2 or 3 substitutions.

In another embodiment, the oligonucleotide of the invention comprises a contiguous sequence complementary to a sequence selected from the group consisting of 8 contiguous bases, 9 contiguous bases, 10 contiguous bases, 11 contiguous bases, 12 contiguous bases, 13 contiguous bases, 14 contiguous bases, 15 contiguous bases, 16 contiguous bases, 17 contiguous bases, 18 contiguous bases, 19 contiguous bases, 20 contiguous bases, 21 contiguous bases, 22 contiguous bases, 23 contiguous bases, 24 contiguous bases, 25 contiguous bases, 30 contiguous bases, and 35 contiguous bases of any of SEQ ID NO:1-56 or any of SEQ ID NO:1-56 comprising 1, 2 or 3 substitutions.

Even more preferably, oligonucleotide of the invention comprises a contiguous sequence selected from the group consisting of 8-25 bases, 10-22 bases and 12-20 bases complementary to any of SEQ ID NO:1-56 or any of SEQ ID NO:1-56 comprising 1, 2 or 3 substitutions.

Thus, contiguous base pairs can be formed between the oligonucleotide of the invention and any of SEQ ID NO:1-56 or any of SEQ ID NO:1-56 comprising 1, 2 or 3 substitutions.

Preferably, consecutive base pairing include positions 22-27 of any of SEQ ID NO:1-56 or any of SEQ ID NO:1-56 comprising 1, 2 or 3 substitutions. I.e. preferably, the oligonucleotide of the invention comprise a contiguous sequence complementary to position 22-27 of SEQ ID NO:1-56 or any of SEQ ID NO:1-56 comprising 1, 2 or 3 substitutions.

Consecutive base pairing covering position 22-27 is important because this region corresponds to the seed region of a microRNA. In one embodiment, base pairing ends at position 27. In other embodiments, base pairing ends respectively at position 28, 29, 30, 31, 32 and 33.

In another embodiment, base pairing starts at position 22. In other embodiments, base pairing starts respectively at position 21, 20, 19, 18, 17, 16, 15, 14, 13, 12, 11, 10, 9, 8, 7, 6 and 5.

In still another embodiment, base pairing includes positions 8-28, 8-27, 9-27, 10-27, 11-27, 12-27, 13-27, 14-27, 15-27, 16-27, 17-27, 18-27, 19-27, 20-27, 21-27, 9-28, 10-28, 11-28, 12-28, 13-28, 14-28, 15-28, 16-28, 17-28, 18-28, 19-28, 20-28 and 21-28.

Length of Oligonucleotide

As is also outlined in the examples section, the oligonucleotides can be adjusted in length to fulfil various criteria. For strong binding to its target RNA, the length may be increased. In some cases, delivery into cells may be improved may using shorter oligonucleotides. Further, in other cases, the position of the oligonucleotide respectively to the antiseed sequence of the target RNA may be adjusted, i.e. the position of bases complementary to position 22-27 of the target RNAs of table 1 (SEQ ID NO:1-56) may be adjusted such that they are placed e.g. at the 5'end of oligonucleotide, at the 3'end or in the middle of the oligonucleotide. Preferably, the position of bases complementary to position 22-27 are placed in the oligonucleotide such that they start at position 1, position 2, position 3, position 4, position 5 or position 6, or at a position upstream of position 2, position 3, position 4, position 5 or position 6 or at a position downstream of position 1, position 2, position 3, position 4, position 5 or position 6, wherein the positions are counted from the 5'end of the oligonucleotide Preferably, the oligonucleotides of the invention are between 8 and 25 bases in lengths. Even more preferably, the oligonucleotides of the invention are between 10 and 20 bases in length.

Substitutions

In one embodiment, any of SEQ ID NO:1-56 may comprise 1 or 2 substitutions.

In yet another one embodiment, any of SEQ ID:NOs:1-56 may comprise only 1 substitution.

In a further embodiment, any of SEQ ID NO:1-56 may not comprise any substitutions.

In yet another embodiment, the substitutions of any of SEQ ID NO:1-56 are located in the region of complementarity between the oligonucleotide of the invention and any of SEQ ID NOs:1-56.

Substitutions may be present in any of SEQ ID NO:1-56 for various reasons. They may e.g. be SNPs that may enhance or decrease microRNA regulation of the given target RNA. An SNP may even create a new micro RNA target site such as to cause aberrant microRNA regulation of the given target RNA. Also RNA editing may give rise to substitutions.

In still another embodiment, only 1 substitution may be present in position 22-27 of any of SEQ ID NOs:1-56. In this embodiment, further substitutions may be present else where in the target sequence. Thus, there may e.g. be one substitution in position 22-27 and one or two more substitutions elsewhere in the target RNA (any of SEQ ID NOs:1-56).

Activity of the Oligonucleotides of the Invention

RNase H Activation

In one embodiment of the invention, the oligonucleotide is capable of activating RNase H. RNase H will cleave the RNA part of a RNA-DNA duplex and the structural requirements for RNase H activation are well-known to the skilled man. This mechanism is very often used to achieve traditional antisense regulation e.g. by employing so-called gapmers. Gapmers are antisense oligonucleotides that comprise a central region with deoxy sugars (the gap) and modified flanks. Gapmers very often comprises phosphorothioate internucleotide linkages to improve biostability and the flanks comprise e.g. 2-O-modifications that also improve biostability, i.e. resistance against nucleolytic attack. The flanks may also comprise modifications that increase the melting temperature of the gapmer base paired to a complementary nucleic acid. Some 2-O-modifications (e.g. 2-O-Methyl and LNA) at the flanks are capable of both improving biostability and increasing the melting temperature of the gapmer base paired to a complementary nucleic acid.

Thus, in one preferred embodiment, the oligonucleotide of the invention comprises a contiguous sequence of deoxynucleotides of at least units to enable RNase H activation and hence cleavage of the target RNA. Even more preferably, 6, 7, or 8 contiguous deoxynucleotides should be present.

In another embodiment, the oligonucleotide of the invention is not capable of activating RNase H. In this embodiment, the oligonucleotide does not comprise a contiguous sequence of unmodified DNA that exceeds a length selected from the group consisting of: 3 bases, 4 bases, 5 bases, 6 bases, 7 bases, 8 bases, 9 bases, 10 bases and 11 bases. Most preferably, the stretch of unmodified DNA does not exceed 3 bases. The skilled man will easily be able to test whether a given oligonucleotide does indeed activate RNase H.

RNAi Activation

The RNAi machinery is a sophisticated gene regulatory system that is guided by RNA. Thus, microRNAs guide the RNAi machinery to target mRNAs (or other target RNAs such as viral target RNAs) to affect the activity of the target mRNA. The RNAi machinery may affect translation of the mRNA directly or it may affect the stability of the target mRNA, i.e. mediate direct degradation of the target mRNA. Not intended to be bound by theory, it is believed that the degree of complementarity between microRNA and target mRNA is a key element as to whether the target mRNA is subjected to translational regulation or degradation.

Endogenous microRNAs are processed from precursor stem-loops and incorporated into a so called RNA induced silencing complex (RISC complex). The details of this process are still poorly understood.

The cellular RNAi machinery has been extensively used to affect the activity of cellular mRNAs by introducing synthetic double stranded RNA complexes termed siRNAs into the cell. As mentioned above, siRNAs are short double stranded RNA complexes comprising a passenger strand and a complementary guide strand. The guide strand of siRNA is incorporated into the RISC complex, where after the RISC complex can affect the activity of mRNA harbouring complementary sequences to the guide strand. Thus, siRNAs are a new class of compounds that is thought to be capable of efficiently and specifically targeting any mRNA and consequently, siRNAs are regarded potentially as a new class of therapeutics.

A common feature of siRNAs and microRNAs is that they recruit the cellular RNAi machinery to affect the activity of target RNAs.

In one embodiment, the oligonucleotides of the invention are capable of recruiting the RNAi machinery and directing the RNAi machinery to the target RNA. This may result in cleavage of the target RNA or translational repression of the target RNA. In this embodiment, the oligonucleotide may be a siRNA. I.e. the oligonucleotide is hybridised to a complementary oligonucleotide, typically over a length of 20-22 bases and very often with 3'overhangs of 1-3 bases. The oligonucleotide may also act as a microRNA, without being identical to a naturally occurring microRNA. Where naturally occurring microRNAs typically regulates many target RNAs, a oligonucleotide of the invention acting as a microRNA may be designed to only regulate a few target RNAs or only one target RNA. Gene specific oligonucleotides of the invention functioning as a microRNA may e.g. be capable of base pairing to position 22-28 of any of SEQ ID NOs: 1-56 and e.g. also to position 7-16 or position 7-18.

Oligonucleotides of the invention designed for RNaseH activation or for RNAi activation will be more potent than an average oligonucleotide designed for RNaseH activation or RNAi activation, because they target a microRNA target site, which has evolved for interaction via an antisense mechanism and is consequently more accessible than average sites.

Blockmir

In another embodiment, the oligonucleotides of the invention cannot recruit the RNAi machinery. In this embodiment, it is preferred that the oligonucleotides of the invention are capable of blocking the activity of the RNAi machinery at a particular target RNA. The oligonucleotides may do so by sequestering the target sequence (micro RNA binding site) of the target RNA, such that the RNAi machinery will not recognize the target sequence, as it is base paired to an oligonucleotide of the invention. Oligonucleotides of the invention with this activity may also be referred to as blockmirs, because they block the regulatory activity of a given microRNA at a particular target RNA.

Thus, in a preferred embodiment, the oligonucleotide is capable of blocking the regulatory activity of a microRNA at a particular target RNA. Preferably, the microRNA is an endogenous microRNA.

If the microRNA is a positive regulator of the target RNA, the oligonucleotide will be a negative regulator of the target RNA.

Most often, the microRNA is a negative regulator of the target RNA. Thus, in another embodiment, the oligonucleotide is a positive regulator of the target RNA and thus enhances the activity of the target RNA. This is contrary to traditional antisense oligonucleotides, microRNAs and siRNAs that typically act as negative regulators by mediating translational repression and/or degradation of the target RNA.

Off-target Effects

In most embodiments, off-target binding of the blockmir will have very few or no effects. This is contrary to antimirs, RNAi mediated by siRNAs and microRNAs, and RNase H mediated antisense regulation, which may all give rise to off-target effects. The blockmir only has an effect if it binds to its intended target, i.e. a microRNA target region and thereby prevents microRNA regulation of the target RNA.

Thus, in a preferred embodiment, the blockmir will have reduced off-target effects, as compared to regulating the activity of the target mRNA using an antimir.

An antimir, as used in the present context, is an oligonucleotide that can base pair with a microRNA and thereby inhibit the activity of the microRNA. Since most microRNAs are promiscuous, i.e. they regulate more than one target, regulation of a particular microRNA will affect the activity of more than one target mRNA. Thus, when it is desired to only regulate the activity of one particular target mRNA, regulation of other target mRNAs may be referred to as off-target effects of the antimir. Such effects could also be referred to as non-intended effects or side effects of the antimir.

Using a microRNA to affect or regulate the activity of a target mRNA, instead of an antimir will obviously also have off-target effects.

In conclusion, blockmirs of the present invention are characteristic in that they affect the activity of a target RNA by preventing microRNA regulation of the target RNA. Thus, blockmirs of the present invention will have reduced off target effects as compared to both traditional antisense oligonucleotides, antimirs, and RNAi mediated regulation using microRNAs and siRNAs.

Architecture and Chemistry

The activity of the oligonucleotide of the invention can be affected by architecture and chemistry.

Thus, different modifications may be placed at different positions to prevent the oligonucleotide from activating RNase H and/or being capable of recruiting the RNAi machinery. In another embodiment, they may be placed such as to allow RNase H activation and/or recruitment of the RNAi machinery.

As referred to herein, any non-natural nucleotides are referred to as modifications of the oligonucleotide. The modifications may be non-natural bases, e.g. universal bases. It may be modifications on the backbone sugar or phosphate, e.g. 2'-O-modifications including LNA or phosphorothioate linkages. As used herein, it makes no difference whether the modifications are present on the nucleotide before incorporation into the oligonucleotide or whether the oligonucleotide is modified after synthesis.

Preferred modifications are those that increase the affinity of the oligonucleotide for complementary sequences, i.e. increases the tm (melting temperature) of the oligonucleotide base paired to a complementary sequence.

Such modifications include 2'-O-Flouro, 2'-O-methyl, 2'-O-methoxyethyl. Also the use of LNA (locked nucleic acid) units, PNA (peptide nucleic acid) units or INA (intercalating nucleic acid) units is preferred. For shorter oligonucleotides, it is preferred that a higher percentage of affinity increasing modifications are present. If the oligonucleotide is less than 12 or 10 units long, it may be composed entirely of LNA units.

Preferred are also modifications that increase the biostability of the oligonucleotide, which also includes 2'-O-Flouro, 2'-O-methyl, 2'-O-methoxyethyl. Also the use of LNA (locked nucleic acid) units, PNA (peptide nucleic acid) units or INA (intercalating nucleic acid) units is preferred.

A wide range of other non-natural units may also be build into the oligonucleotide. E.g. morpholino, 2'-Deoxy-2'-fluoro-arabinonucleic acid (FANA) and arabinonucleic acid (ANA).

In a preferred embodiment, the fraction of units modified at either the base or sugar relatively to the units not modified at either the base or sugar is selected from the group consisting of less than less than 99%, 95%, less than 90%, less than 85% or less than 75%, less than 70%, less than 65%, less than 60%, less than 50%, less than 45%, less than 40%, less than 35%, less than 30%, less than 25%, less than 20%, less than 15%, less than 10%, and less than 5%, less than 1%, more than 99%, more than 95%, more than 90%, more than 85% or more than 75%, more than 70%, more than 65%, more than 60%, more than 50%, more than 45%, more than 40%, more than 35%, more than 30%, more than 25%, more than 20%, more than 15%, more than 10%, and more than 5% and more than 1%.

Lipids and/or peptides may also be conjugated to the oligonucleotide. Such conjugation may both improve bioavailability and prevent the oligonucleotide from activating RNase H and/or recruiting the RNAi machinery. Conjugation of larger bulkier moieties is preferably done at the central part of the oligonucleotide, e.g. at any of the most central 5 units. Alternatively, at one of the bases complementary to one of position 22-27 of any of SEQ ID NOs 1-56. In yet another embodiment, the moiety may be conjugated at the 5'end or the 'end of the oligonucleotide.

A preferred hydrophobic moiety is cholesterol moiety that may be conjugated to the oligonucleotide and prevent the oligonucleotide from recruiting the RNAi machinery and improve the bioavailability of the oligonucleotide. The cholesterol moiety may be conjugated to at one of the bases complementary to one of position 22-27 of any of SEQ ID NOs 1-56, at the 3'end or the 5'end of the oligonucleotide.

Further, in a preferred embodiment, phosphorothioate internucleotide linkages may connect the units to improve the biostability of the oligonucleotide. All linkages of the oligonucleotide may be phosphorothioate linkages. In another embodiment, the fraction of phosphorothioate linkages is selected from the group consisting of less than 95%, less than 90%, less than 85% or less than 75%, less than 70%, less than 65%, less than 60%, less than 50%, more than 95%, more than 90%, more than 85% or more than 75%, more than 70%, more than 65%, more than 60% and more than 50%.

In yet another embodiment, the oligonucleotide may comprise a mix of DNA units and RNA units such as to prevent the oligonucleotide from activating RNase H and to at the same time prevent the oligonucleotide from recruiting the RNAi machinery. E.g. a DNA unit may be followed by a RNA unit that is again followed by a DNA unit and so on. The DNA units and RNA units may come in blocks. The blocks may have a length of 2 units, 3 units, 4 units, 5 units or 6 units and units of different length may be comprised with the same oligonucleotide.

In another preferred embodiment, the oligonucleotide comprises a mix of LNA units and RNA units with a 2'-O-methyl. Such LNA/2'O-Methyl mixmers have been used as steric block inhibitors of Human Immunodeficiency Virus Type 1 Tat-Dependent Trans-Activation and HIV-1 Infectivity.

Lna-dna

In one embodiment, the oligonucleotide of the invention does not comprise any RNA units. Few or no RNA units may be used to prevent the oligonucleotide from being capable of recruiting the RNAi machinery. As outlined above, chemical modifications/non-natural units can do the same. One such example is a oligonucleotide comprising LNA units and DNA units. In a preferred embodiment, the oligonucleotide comprises exclusively LNA units and DNA and these may be connected by phosphorothioate linkages as outlined above.

In another embodiment, the oligonucleotide of the invention does not comprise any DNA units.

In still another embodiment, the oligonucleotide of the invention does not comprise any morpholino units and/or LNA units.

In a preferred embodiment, the oligonucleotides comprise a number of nucleotide units that increase the affinity for complementary sequences selected from the group of: at least 1 units, at least 2 units, at least 3 units, at least 4 units, at least 5 units, at least 6 units, at least 7 units, at least 8 units, at least 9 units, at least 10 units, at least 11 units, at least 12 units, at least 13 units, at least 14 units, at least 15 units, at least 16 units, at least 17 units, at least 18 units, at least 19 units, at least 20 units, at least 21 units, and at least 22 units.

In another preferred embodiment, the oligonucleotides comprise a number of nucleotide units that increase the affinity for complementary sequences selected from the group of: no more than 1 units, no more than 2 units, no more than 3 units, no more than 4 units, no more than 5 units, no more than 6 units, no more than 7 units, no more than 8 units, no more than 9 units, no more than 10 units, no more than 11 units, no more than 12 units, no more than 13 units, no more than 14 units, no more than 15 units, no more than 16 units, no more than 17 units, no more than 18 units, no more than 19 units, no more than 20 units, no more than 21 units, and no more than 22 units.

In a yet another preferred embodiment, the oligonucleotides comprise a number of nucleotide units that increase the affinity for complementary sequences selected from the group of: 1 units, 2 units, 3 units, 4 units, 5 units, 6 units, 7 units, 8 units, 9 units, 10 units, 11 units, 12 units, 13 units, 14 units, 15 units, 16 units, 17 units, 18 units, 19 units, 20 units, 21 units, and 22 units.

In a preferred embodiment, nucleotide units that increase the affinity for complementary sequences are located at the flanks of the oligonucleotide. E.g. if the oligonucleotide comprise e.g. 10 LNA units, 5 may be located at the 5'end and the other 5 units may be located at the 3'end. In another embodiment, the nucleotide units that increase the affinity for complementary sequences are at the central portion of the oligonucleotide. Thus, if the oligonucleotide has a length of 18 units of which 8 are LNA units, 5 natural units may be followed by 8 LNA units again followed by 5 natural units.

The nucleotide units that increase the affinity for complementary sequences may also be distributed evenly over the length of the oligonucleotide. E.g. at every 2, 3, 4, 5, 6 positions or any combinations thereof.

Single-stranded Vs. Double Stranded

The oligonucleotide of the invention is preferably not base paired with a complementary oligonucleotide or intended for use a base paired with a complementary oligonucleotide. I.e. it should be single stranded to facilitate interaction with a target RNA and in certain embodiments, also to prevent recruitment of the RNAi machinery.

In another embodiment, the oligonucleotide is base paired to a complementary oligonucleotide. This may e.g. be the case when the oligonucleotide is acting as a siRNA or a microRNA and/or it it may also be used to improve delivery of the oligonucleotide. Thus, in one embodiment, the oligonucleotide is base paired to a RNA molecule that is degraded by RNase H, when the oligonucleotide enters its target cell. In this way, the oligonucleotide is liberated on site.

Specific Sequences

In still another embodiment of the invention, the target sequence resides within the 5'noncoding region of hepatitis C virus as outlined in example 3. The target sequence is as shown in example 3 (5'GCCAGCCCCCUGAUGGGGGC-GACACUCCACCAUAGAUCAC). In this embodiment, the oligonucleotide is capable of basepairing the target sequence over a stretch of nucleotides selected from the group consisting of 25 bases, 24 bases, 23 bases, 22 bases, 21 bases, 20 bases, 19 bases, 18 bases, 17 bases, 16 bases, 15 bases, 14 bases, 13 bases, 12 bases, 11 bases, 10 bases, 8 bases, 7 bases and 6 bases.

Preferably, the X mir (blockmir) covers at least the antiseed sequence of the target sequence and will thus be able to prevent mir-122 in interacting with the antiseed sequence. The antiseed sequence is complementary to the seed sequence of mir-122, i.e. complementary to at least position 2-8 of mir-122.

Such an oligonucleotide will be useful for treatment of hepatitis virus C infection and also on the study of mir-122 facilitated HCV replication. Importantly, the oligonucleotide will not affect the expression of other mir-122 targets as would be the case if a mir-122 antagomir is employed.

A second aspect of the invention is a method of modulating the activity of a target RNA comprising the steps of:
  a. Providing a system comprising a target RNA
  b. Introducing an oligonucleotide of the invention that targets the target RNA to the system
  c. Thereby modulating the activity of the target RNA Preferably, the oligonucleotide prevents the activity of a microRNA at the target RNA and thereby regulates the activity of the target RNA.

In another embodiment, the oligonucleotide induces RNase H cleavage of the target RNA and thereby regulates the activity of the target RNA.

In yet another embodiment, the oligonucleotide induces RNAi degradation of the target RNA and thereby regulates the activity of the target RNA.

In a preferred embodiment of the second aspect of the invention, the system is either a cell extract or a cell In another preferred embodiment of the second aspect of the invention, the method is performed in vivo, ex vivo or in vitro.

Pharmaceutical Composition and Treatment

A third aspect of the invention is a pharmaceutical composition comprising the oligonucleotide of the invention. As the skilled man will understand from the above description, the oligonucleotide may be used for therapy in the same manner as siRNAs, microRNAs and antisense oligonucleotides, because they can be used to specifically affect the expression of a particular gene. Specific disease areas and conditions are described in the examples section.

A fourth aspect of the invention is a method of treatment comprising administering the oligonucleotide of the invention or the pharmaceutical composition of the invention to a person in need thereof.

A fifth aspect of the invention is the oligonucleotide of the invention for use as medicine.

A sixth aspect of the invention is use of the oligonucleotide of the invention for the preparation of a medicament for treatment of cancer, viral infection, immunological disease or cardiovascular disease.

A seventh aspect of the invention is use of the oligonucleotide for modulating the activity of a target RNA.

EXAMPLES

Example 1

An Xmir (blockmir) targeting Mtpn useful for treatment of diabetes

It has been demonstrated that mir-375 is a regulator of pancreatic island insulin secretion, and that Myotrophin (Mtpn) is a target of mir-375 regulation (Poy M N, 2004). Further, it has been shown that siRNA inhibition of Mtpn mimics the effects of miR-375 on glucose stimulated insulin secretion and exocytosis. Thus, it was concluded by the authors that miR-375 is a regulator of insulin secretion and may thereby constitute a novel pharmacological target for the treatment of diabetes.

Here we provide Xmirs that can regulate Mtpn expression by inhibiting mir-375 regulation of Mtpn activity on the 3'UTR of the Mtpn mRNA.

The relevant portion of the target mRNA is:

5' GUGUUUUAAGUUUUGUGUUGCAAGAACAAAUGGAAUAAACUUGAAU

The anti-seed sequence is shown in bold. This target region of the target RNA can be identified e.g. by searching the target RNA for anti-seed sequences. Or the target region can be found using suitable databases available on the internet e.g. http://pictar.bio.nyu.edu, www.targetscan.org, http://microrna.sanger.ac.uk.

Obviously, the information may also be available from experiments or from a scientific publication (as e.g. Poy et al., 2004)

The sequence of mir-375 is:

5' UUUGUUCGUUCGGCUCGCGUGA

Pairing the seed sequence to the anti-seed sequence gives e.g. the following interactions.

```
5'  ...AGUUUUGUGUUGC---AAGAACAAAU...
       |:|  ||    ||||||
    3' AGUGCGC-UCGGCUUGCUUGUUU
```

It is seen that overall complementarity is scarce.
The Xmir:

An Xmir capable of regulating Mtpn expression by inhibition of mir-375 regulation will have to be able to sequester the anti-seed sequence of the target region, i.e. hide the anti-seed sequence in base pairing.

Thus, Xmirs (lower strand in 3'-5' direction) of Mtpn are exemplified here, base paired to the target sequence (upper strand in 5'-3' direction):

5' GUGUUUUAAGUUUUGUGUUGCAAGAACAAAUGGAAUAAACUUGAAU
    ||||||||||||||||||||||||||||||||||||||||
   GUUCAAAACACAACGUUCUUGUUUACCUUAUUUG

5' GUGUUUUAAGUUUUGUGUUGCAAGAACAAAUGGAAUAAACUUGAAU
    |||||||||||||||||||||||||||||||||||||
   GUUCAAAACACAACGUUCUUGUUUACCUU

5' GUGUUUUAAGUUUUGUGUUGCAAGAACAAAUGGAAUAAACUUGAAU
    ||||||||||||||||||||||||||||||
   GUUCAAAACACAACGUUCUUGUUU

5' GUGUUUUAAGUUUUGUGUUGCAAGAACAAAUGGAAUAAACUUGAAU
    |||||||||||||||||||||||||||
   CAAAACACAACGUUCUUGUUUGCC

5' GUGUUUUAAGUUUUGUGUUGCAAGAACAAAUGGAAUAAACUUGAAU
    |||||||||||||||||||||
   CACAACGUUCUUGUUUGCC

5' GUGUUUUAAGUUUUGUGUUGCAAGAACAAAUGGAAUAAACUUGAAU
    |||||||||||||||||
   CAACGUUCUUGUUUACC

5' GUGUUUUAAGUUUUGUGUUGCAAGAACAAAUGGAAUAAACUUGAAU
    ||||||||||||||||
   CGUUCUUGUUUACC

5' GUGUUUUAAGUUUUGUGUUGCAAGAACAAAUGGAAUAAACUUGAAU
    ||||||||||||||
   GUUCUUGUUUACC

5' GUGUUUUAAGUUUUGUGUUGCAAGAACAAAUGGAAUAAACUUGAAU
    ||||||||||||
   GUUCUUGUUUAC

5' GUGUUUUAAGUUUUGUGUUGCAAGAACAAAUGGAAUAAACUUGAAU
    |||||||||||
   GUUCUUGUUA

5' GUGUUUUAAGUUUUGUGUUGCAAGAACAAAUGGAAUAAACUUGAAU
    ||||||||
   CUUGUUUA

As for the following examples, this structure can be used to design further blockmirs:

3' AGUGCGCUCGGCUUGCUUGUUU
                  |||||||
5' GUUUUAAGUUUUGUGUUGCAAGAACAAAUGGAAUAACUU
   |||||||||||||||||||||||||||||||||||||||
3' CAAAATTCAAAACACAACGTTCTTGTTTACCTTATTGAA

The upper strand is the microRNA, the middle strand is the target RNA and the lower strand is a blockmir that can be truncated at both ends.

The Xmirs designed above may be synthesized using methods known in the art. As described in the specification, they may be synthesised as DNA, RNA, LNA, INA or with mixed monomers.

Obviously, U monomers may be exchanged with T monomers, while still allowing base pairing. Also G-C base pairs may be substituted with G-U wobble base pairs.

Methods for synthesizing various embodiments of the above designed Xmirs targeting the Mtpn mRNA are well known to the skilled man within the field of oligonucleotide synthesis. Particular preferred embodiments are described in the detailed description of the invention.

Conjugation of the Xmirs to e.g. cholesterol is also within the common knowledge of the skilled man.

Example 2

Xmirs Targeting TGF-beta and SMAD3 for treatment of Herpes-simplex Virus Infection Recently it was demonstrated that Herpes simplex virus-1 encodes a microRNA that enables the virus to establish a latent infection (Gupta A, 2006). The microRNA that was termed mir-LAT was found to regulate TGF-beta and SMAD3, and thereby affect the ability of the cell to undergo apoptosis, the usual process by which an infected cell self-destructs in order to prevent production of viral progeny. Thus, it is of interest to be able to block the regulatory activity of mir-LAT on the expression of TGF-beta and SMAD3.

The sequence of the target region of the TGF-beta mRNA is:

```
5'AGGTCCCGCCCCGCCCCGCCCCGCCCCGGCAGGCCCGGCCCCACC
```

The sequence of mir-LAT is:

```
5'UGGCGGCCCGGCCCGGGGCC
```

Thus, the following complex may be formed:

```
5'CGCCCCGGCAGGCCCGGCC-CCA
   |||||||   |||  ||||  |||
3'CCGGGGCC---CGGCCCGGCGGU
```

A series of Xmirs can be designed as was also done in the previous example. The lower strand is the Xmir shown in the 3'-5' direction and the upper strand is the target region of TGF-beta mRNA:

```
5' AGGUCCCGCCCCGCCCCGCCCCGCCCCGGCAGGCCCGGCCCCACC
   |||||||||||||||||||||||||||||||||||||||||||||
   UCCAGGGCGGGGCGGGGCGGGGCGGGGCCGUCCGGGCCGGGGUGG

5' AGGUCCCGCCCCGCCCCGCCCCGCCCCGGCAGGCCCGGCCCCACC
   |||||||||||||||||||||||||||||||||||||||||
      GGGGCGGGGCGGGGCGGGGCCGUCCGGGCCGGGGUGG

5' AGGUCCCGCCCCGCCCCGCCCCGCCCCGGCAGGCCCGGCCCCACC
   |||||||||||||||||||||||||||||||||||||
          GGCGGGGCGGGGCCGUCCGGGCCGGGGUGG

5' AGGUCCCGCCCCGCCCCGCCCCGCCCCGGCAGGCCCGGCCCCACC
   |||||||||||||||||||||||||||||||||
              GCGGGGCCGUCCGGGCCGGGGUGG
```

As for the following examples, this structure can be used to design further blockmirs:

```
         CCGGGGCCCGGCCCGGCGGU
             |||| |||
5' CCGCCCCGCCCCGGCAGGCCCGGCC-CCACCCCGCCCCGCC
   |||||||||||||||||||||||| |||||||||||||||
   GGCGGGGCGGGGCCGTCCGGGCCGG-GGTGGGGCGGGGCGG
```

The upper strand is the microRNA, the middle strand is the target sequence, and the lower strand is an exemplary blockmir that can be truncated at both ends.

Synthesis of various embodiments of such sequences is well within the ability of the skilled man. Particular preferred embodiments are described in the detailed description of the invention.

Example 3

An Xmir Targeting HCV for Treatment of Hepatitis C Infection

Background

It has been demonstrated that mir-122 modulates Hepatitis C virus RNA abundance by facilitating replication of the viral RNA (Jopling CL, 2005).

The HCV genome comprises a conserved antiseed sequence capable of base pairing with the seed sequence of mir-122 in both the 3'noncoding region and the 5'noncoding region.

Further, it was demonstrated that the level of HCV viral replicon RNA was reduced by app. 80% when mir-122 was inactivated by a so-called antagomir.

A genetic interaction between mir-122 and the 5' noncoding region of the viral genome was revealed by mutational analysis of the predicted micro RNA binding site and ectopic expression of mir-122 molecules containing compensatory mutations.

The authors suggest that an antagomir targeting mir-122 may be used for antiviral therapy.

Blockmirs Targeting HCV

The sequence of the target region (anti-seed sequence is bold) in the 5'noncoding region is:

```
5'GCCAGCCCCUGAUGGGGGCGACACUCCACCAUAGAUCAC
```

The sequence of mir-122 with the seed sequence underlined:

```
3'UGUUUGUGGUAACAGUGUGAGGU
```

Base-pairing between seed and antiseed:

```
5' GCCAGCCCCUGAUGGGGGCGACACUCCACCAUAGAUCAC
                        |||||||
                3' UGUUUGUGGUAACAGUGUGAGGU
```

Thus, Xmirs of HCV are exemplified here (basepaired to the target region of HCV):

```
5' GCCAGCCCCUGAUGGGGGCGACACUCCACCAUAGAUCAC
   |||||||||||||||||||||||||||||||||||||||
   CGGTCGGGGACTACCCCCGCTGTGAGGTGGTATCTGGTG

5' GCCAGCCCCUGAUGGGGGCGACACUCCACCAUAGAUCAC
   |||||||||||||||||||||||||||||||||||
   CGGTCGGGGACTACCCCCGCTGTGAGGTGGTATC

5' GCCAGCCCCUGAUGGGGGCGACACUCCACCAUAGAUCAC
   ||||||||||||||||||||||||||||||||||
   CGGTCGGGGACTACCCCCGCTGTGAGGTGGTA

5' GCCAGCCCCUGAUGGGGGCGACACUCCACCAUAGAUCAC
   |||||||||||||||||||||||||||||||
   CGGTCGGGGACTACCCCCGCTGTGAGGTG

5' GCCAGCCCCUGAUGGGGGCGACACUCCACCAUAGAUCAC
   ||||||||||||||||||||||||||||||
   CGGTCGGGGACTACCCCCGCTGTGAGG

5' GCCAGCCCCUGAUGGGGGCGACACUCCACCAUAGAUCAC
   ||||||||||||||||||||||||||||||||||
      GGGGACTACCCCCGCTGTGAGGTGGTATCTGGTG

5' GCCAGCCCCUGAUGGGGGCGACACUCCACCAUAGAUCAC
   |||||||||||||||||||||||
           TACCCCCGCTGTGAGGTGGTA
```

-continued

```
5' GCCAGCCCCCUGAUGGGGGCGACACUCCACCAUAGAUCAC
         ||||||||||||||||||
         CTACCCCCGCTGTGAGGTG

5' GCCAGCCCCCUGAUGGGGGCGACACUCCACCAUAGAUCAC
         ||||||||||||||||||
         GGACTACCCCGCTGTGAGG

5' GCCAGCCCCCUGAUGGGGGCGACACUCCACCAUAGAUCA
         |||||||||||||||
         CCCCCGCTGTGAGG

5' GCCAGCCCCCUGAUGGGGGCGACACUCCACCAUAGAUCAC
              |||||||||
              GCTGTGAGG
```

The Xmir may be either DNA or RNA, i.e. T may be substituted for U. Other embodiments are described in the detailed description of the invention.

Example 4

Blockmirs Useful for Treatment of Psoriasis

It has been demonstrated that psoriasis is characterized by a specific miRNA expression profile that differs from that of healthy skin or another chronic inflammatory disease, atopic eczema. Among miRNAs overexpressed in psoriasis, a keratino cytespecific miRNA (miR-203) and a leukocyte-derived miRNA (miR-146a) were identified.

The up-regulation of miR-203 in psoriatic plaques was concurrent with the down-regulation of an evolutionary conserved target of miR-203, suppressor of cytokine signaling 3 (SOCS-3), which is involved in inflammatory responses and keratinocytefunctions (Sonkoly E, 2007, Jul. 11).

Another study showed that miR-146a, one of the psoriasis-specific miRNAs, inhibits the expression of IRAK-1 (interleukin-1 receptor-associated kinase 1) and TRAF-6 (TNF receptor-associated factor 6) proteins both of which are regulators of the TNF-a signalling pathway (Taganov K D, 2006). Hence, it is conceivable that miR-146a is involved in the pathogenesis of psoriasis via the modulation of TNF-a signalling in the skin.

Blockmirs for Treatment of Psoriasis
SOCS-3:
The target region of the SOCS-3 mRNA is:

```
5'UAUUUAUAUUCAGAAAAGAAACAUUUCAGUAAUUUAUAAU
```

Complementarity to mir-203 (upper strand) is shown here, as is also a potential blockmir (lower strand):

```
              GAUCACCAGGAUUUGUAAAGUG
                     |||||||||||
5' UAUUUAUAUUCAGAAAAGAAACAUUUCAGUAAUUUAUAAU
   |||||||||||||||||||||||||||||||||||||||
   ATAAATATAAGTCTTTTCTTTGTAAAGTCATTAAATATTA
```

Further exemplary blockmirs are shown here base paired to the target region of the SOCS-3 mRNA:

```
5' UAUUUAUAUUCAGAAAAGAAACAUUUCAGUAAUUUAUAAU
   |||||||||||||||||||||||||||||||||||||||
   ATAAATATAAGTCTTTTCTTTGTAAAGTCATTAAATATTA

5' UAUUUAUAUUCAGAAAAGAAACAUUUCAGUAAUUUAUAAU
   |||||||||||||||||||||||||||||||||||||
   ATAAATATAAGTCTTTTCTTTGTAAAGTCATTAA

5' UAUUUAUAUUCAGAAAAGAAACAUUUCAGUAAUUUAUAAU
   |||||||||||||||||||||||||||||||||||
   ATAAGTCTTTTCTTTGTAAAGTCATTAAATATTA

5' UAUUUAUAUUCAGAAAAGAAACAUUUCAGUAAUUUAUAAU
      |||||||||||||||||
      TTTTCTTTGTAAAGTCATTAA

5' UAUUUAUAUUCAGAAAAGAAACAUUUCAGUAAUUUAUAAU
         |||||||||||
         CTTTGTAAAGTC

5' UAUUUAUAUUCAGAAAAGAAACAUUUCAGUAAUUUAUAAU
         |||||||||
         TTTGTAAAGT

5' UAUUUAUAUUCAGAAAAGAAACAUUUCAGUAAUUUAUAAU
           |||||||
           GTAAAGT
```

The Blockmir may be either DNA or RNA, i.e. T may be substituted for U. Other embodiments are described in the detailed description of the invention.

Likewise, blockmirs can be prepared that prevents mir-146 binding to Irak1 and Traf-6. Obviously, the blockmirs can be truncated and modified as described in the detailed description.

Traf-6 base paired to mir-146 and a blockmir:

```
                    UUGGGUACCUUAAGUCAAGAGU
                              ||||||||
5' CAUAAUCCUUGGAAAACUUAAGUUCUCAUUCACCCCAGUU
   |||||||||||||||||||||||||||||||||||||||
   GTATTAGGAACCTTTTGAATTCAAGAGTAAGTGGGGTCAA
```

Irak-1 base paired to mir-146 and a blockmir:

```
                    UUGGGUACCUUAAGUCAAGAGU
                              ||||||||
5' CCCCCAAAUCCGGAAGUCAAAGUUCUCAUGGUCAGAAGUU
   |||||||||||||||||||||||||||||||||||||||
   GGGGGTTTAGGCCTTCAGTTTCAAGAGTACCAGTCTTCAA
```

Further embodiments of the blockmirs are described in the detailed description of the invention.

Example 5

Blockmirs targeting p27Kip1 useful for treatment of cancer Levels of p27Kip1, a key negative regulator of the cell cycle, are often decreased in cancer. In most cancers, levels of p27Kip1 mRNA are unchanged and increased proteolysis of the p27Kip1 protein is thought to be the primary mechanism for its down regulation. It was recently demonstrated that p27Kip1 protein levels are also down regulated by Mir-221 and mir-222 in glioblastoma and prostate carcinoma (le Sage C, 2007) (Galardi S, 2007) (Gillies 3K, 2007) and the microRNAs was suggested as therapeutic targets.

The sequences of the two microRNAs are:

```
Mir-221
5'AGCUACAUUGUCUGCUGGGUUUC

Mir-222
5'AGCUACAUCUGGCUACUGGGUCUC
```

Two targets of mir-221 and mir-222 were identified. Note that the microRNAs have the same seed sequence and the target region is the same for both microRNAs, i.e. one blockmir can be used to prevent regulation by both microRNAs.

As above, the target sequence is the middle sequence, the upper sequence is the microRNA, the lower sequence is a blockmir. The blockmirs can be truncated and modified as described in the detailed description.

Further putative target regions were identified in the p27Kip1 3'UTR:

Example 6

Blockmirs targeting TPM1 useful for treatment of cancer
TPM1 (Tumor suppressor tropomyosin 1) was recently shown to be targeted by mir-21 (Zhu S, 2007). As the name implies, TPM1 is a tumor suppressor and it was suggested to use mir-21 as a therapeutic target.

The sequence of mir-21 is:

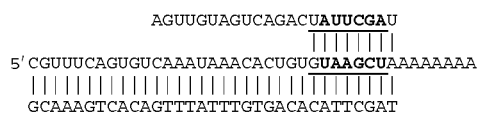

When base paired to the target region:

```
                AGUUGUAGUCAGACUAUUCGAU
                          ||||||||
5' CGUUUCAGUGUCAAAUAAACACUGUGUAAGCUAAAAAAAA
   |||||||||||||||||||||||||||| ||||||||
   GCAAAGTCACAGTTTATTTGTGACACATTCGAT
```

Again the microRNA is the upper sequence, the target region of TPM1 is the middle sequence and a blockmir is shown in the lower sequence. The blockmir may be truncated and modified as described in the detailed description.

Example 7

Blockmir Targeting Lats2 Useful for Treatment of Cancer

It has been demonstrated that mir-372 and mir-373 targets Lats2 (Large tumor suppressor homologue 2) (Voorhoeve P M, 2006). The miRNAs neutralize p53-mediated CDK inhibition, possibly through direct inhibition of the expression of the tumorsuppressor LATS2. Evidence was provided that these miRNAs are potential novel oncogenes participating in the development of human testicular germ cell tumors by numbing the p53 pathway, thus allowing tumorigenic growth in the presence of wild-type p53. Two target regions were identified.

Target 1:

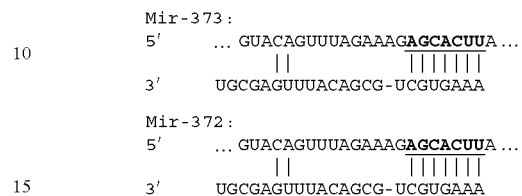

Note, the two microRNAs target the same target region and shares the same seed sequence. Thus, useful blockmirs can be designed from the following alignment:

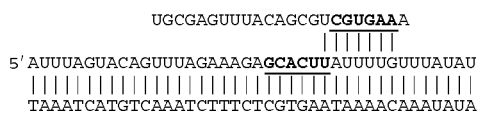

Target 2:

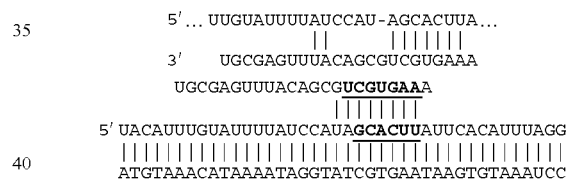

Note that the targets are overlapping for mir-372, mir-373, mir-93, mir302a+b and mir-520.

Example 8

Blockmirs Targeting RB1 and TGFBR2 Useful for Treatment of Cancer

Mir106a vs. RB1

Mir-106a was recently demonstrated to regulate the tumor-suppressors RB1 (Retinoblastoma 1) and TGFBR2 (Transforming growth factor, Beta receptor II) (Voorhoeve P M, 2006).

Mir-106a is shown as the lower strand in the outlined complex:

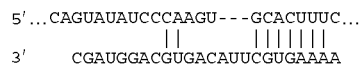

Thus, blockmirs can be designed from the following structures as outlined above.

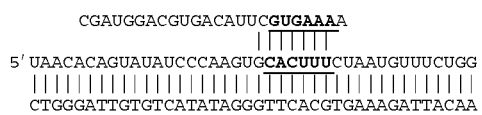

Likewise for Mir-20 vs. TGFBR2:

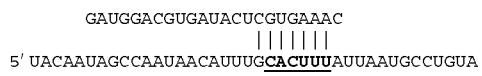

Example 9

Blockmirs Targeting PTEN Useful for Treatment of Cancer

Mir-21 has in several reports been reported to regulate PTEN (Meng F, 2007). PTEN is a tumor suppressor that PTEN suppresses the expression of several MMPs through FAK dephosphorylation. Thus, it is of interest to prevent mir-21 regulation of PTEN. Several potential complexes that may be formed between mir-21 and the 3'UTR of PTEN are listed:

```
1)
mfe: -23.4 kcal/mol
p-value: undefined
position 1816
target 5'   G       UAUAG           A        3'
            CAGCAUU        AGUUUGAU GGC
            GUUGUAG        UCAGACUA UCG
miRNA  3'   A                       U  AU    5'

2)
mfe: -21.9 kcal/mol
p-value: undefined
position 423
target 5'   G     GAUA      CAGUU      A     3'
            CAACA      AGUUUG     GGCUA
            GUUGU      UCAGAC     UCGAU
miRNA  3'   A     AG         UAU        5'

3)
mfe: -21.6 kcal/mol
p-value: undefined
position 2596
target 5'   G     GCUUA   U             C    3'
            CAGCA    CA GUCUGA     AGUUA
            GUUGU    GU CAGACU     UCGAU
miRNA  3'   A     A                  AU      5'

4)
mfe: -20.8 kcal/mol
p-value: undefined
position 1759
target 5'   C     UGU       CCU     A        3'
            UAGC    GGUCUGA     AGUUA
            GUUG    UCAGACU     UCGAU
miRNA  3'   A     UAG       AU              5'

5)
mfe: -18.5 kcal/mol
p-value: undefined
position 86
target 5'   G       U   A   UACC      U      3'
            GACAUUG GUC GAU     AGUUA
            UUGUAGU CAG CUA     UCGAU
miRNA  3'   AG         A   U                5'
```

Full target sequences from which blockmirs can be designed are listed in table 1 and specific embodiments will be apparent from the description.

Example 10

Blockmirs Targeting HIV Useful for Treatment of HIV Infection

Background

It was recently demonstrated that microRNAs play a role in keeping Human Immunodeficiency Virus Type-1 (HIV-1) in a latent state (Huang J, 2007 October; 13(10), Epub 2007 Sep. 30.). The virus can establish a latent state in resting CD4+ T cells, and this latency is a major barrier for the eradication of the virus in patients on suppressive highly active antiretroviral therapy (HAART). The authors of the aforementioned paper found that the 3'UTR of HIV-1 is targeted by a cluster of cellular miRNAs including miR-28, miR-125b, miR-150, miR-223 and miR-382, which are enriched in resting CD4+ T cells as compared to activated CD4+ T cells. Further, it was suggested to use antagomirs to activate latent HIV-1 for therapeutic purposes.

Blockmirs for Activation of Latent HIV-1

Inhibiting multiple microRNAs with antagomirs may have various adverse effects as each microRNA will have a panel of target RNAs. Therefore, we suggest to use blockmirs to specifically disrupt the interaction between the HIV-1 3'UTR and the microRNAs, to thereby activate latent HIV-1 and make the virus susceptible to HAART.

The target sequences are listed next. The microRNA is shown as the upper strand, the target sequence is the middle strand and a blockmir sequence is shown as the lower strand. Specific embodiments of the blockmirs will be apparent from the detailed description of the invention.

Mir-125b:HIV-1 interaction:

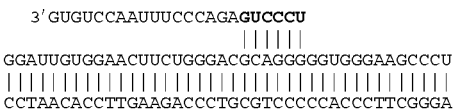

Mir-150: HIV-1 interaction:

Mir-223: HIV-1 interaction:

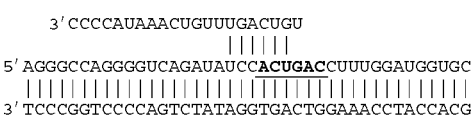

Mir-382: HIV-1 interaction

Mir-28: HIV-1 interaction

```
5' GAGUUAUCUGACACUCGAGGAA
          ||||||
3' AGACCAGAUCUGAGCCUGGGAGCUCUCUGGCUAACUAGGG
   ||||||||||||||||||||||||||||||||||||||||
5' TCTGGTCTAGACTCGGACCCTCGAGAGACCGATTGATCCC
```

The blockmirs for activation of HIV-1 infection may be used individually or in combination. I.e. blockmirs targeting all 5 sequences may be used simultaneously. Alternatively, 4, 3, or 2 target sequences may be targeted simultaneously by blockmirs. Preferably, the same blockmir is used to prevent mir-125b and mir-150 from binding to their target sequences. This is possible, because their target sequences are overlapping.

The blockmirs are preferably used in combination with HAART therapy.

Example 11

Blockmirs for Immune Stimulation

It has been demonstrated that mir-150 is capable of regulating expression of c-myb (Xiao C, 2007 Oct. 5; 131(1)). Inhibition of mir-150 with an antagomir gave rise to various phenotypes such as B1 cell expansion and an enhanced humoral immune response. Thus, serum levels of various antibodies were considerably increased.

The authors suggest that effects of mir-150 on immune stimulation are primarily or even exclusively mediated through regulation of c-myb. We suggest using a blockmir to prevent mir-150 regulation of c-myb upon B and T-cell activation. Hence such blockmir may be used in combination with vaccine to boost the effect of the vaccine or for people with a reduced immune system.

Mir-150 vs. c-myb

Target scan predicts 4 mir-150 targets in the 3'UTR of C-myb. Two of those (listed first as a and b) have been experimentally verified. The target sequences are listed next. The microRNA is shown as the upper strand, the target sequence is the middle strand and a blockmir sequence is shown as the lower strand. Specific embodiments of the blockmirs will be apparent from the detailed description of the invention.

a)
```
3' GUGACCAUGUUCCCAACCCUCU
             |||||||
5' CAAUACAUUUGAAAACUUGUUUGGGAGACUCUGCAUUUUU
   ||||||||||||||||||||||||||||||||||||||||
3' GTTATGTAAACTTTTGAACAAACCCTCTGAGACGTAAAAA
``` b)
```
3' GUGACCAUGUUCCCAACCCUCU
             |||||||
5' GCAUGCGUUGCACUUCUUUUUUGGGAGAUGUGUGUUGUUG
   ||||||||||||||||||||||||||||||||||||||||
3' CGTACGCAACGTGAAGAAAAAACCCTCTACACACAACAAC
``` c)
```
3' GUGACCAUGUUCCCAACCCUCU
             |||||||
5' CAACAUGAAACUUUUCAUGAAUGGGAGAAGAACCUAUUUU
   ||||||||||||||||||||||||||||||||||||||||
3' GTTGTACTTTGAAAAGTACTTACCCTCTTCTTGGATAAAA
``` d)
```
3' GUGACCAUGUUCCCAACCCUCU
             |||||||
5' UAGCCUGACUGUUUUAUAAUUUGGGAGUUCUGCAUUUGAU
   ||||||||||||||||||||||||||||||||||||||||
3' ATCGGACTGACAAAATATTAAACCCTCAAGACGTAAACTA
```

The blockmirs for immune stimulation may be used separately or in combination. Most preferred is a) and b). To achieve the most potent effect, these may be used in combination.

Example 12

Blockmirs for Prevention of Metastatic Breast Cancer

It was recently shown that ectopic miR-10b expression can drive tumour invasion and metastasis in otherwise non-metastatic breast tumours, thereby acting as a potent pro-metastatic agent. Moreover, it was demonstrated that the mRNA encoding homeobox D10 (HOXD10) is a target for mir-10b regulation and that HOXD10 down regulation leads to up regulation of a well characterized pro-metastatic gene, RHOC (Ma L, 2007 Oct. 11; 449(7163), Epub 2007 Sep. 26.). Thus, we propose to block mir-10b regulation of HOXD10 and thereby prevent or reduce metastasis of breast tumours.

Mir-10b vs. HOXD10.

One target in HOXD10 has been experimentally verified. The target sequence is listed next. The microRNA is shown as the upper strand, the target sequence is the middle strand and a blockmir sequence is shown as the lower strand. Specific embodiments of the blockmirs will be apparent from the detailed description of the invention.

```
         UGUUUAAGCCAAGAUGUCCCAU
         ||||   |||||||||
5' AUUAUUUUUUCAUCGUAAUGCAGGGUAACUAUUAUUGCGC
   ||||||||||||||||||||||||||||||||||||||||
3' TAATAAAAAGTAGCATTACGTCCCATTGATAATAACGCG
```

Example 13

Blockmirs for Treatment of CMV Infection

Cytomegalovirus encode microRNAs that facilitate infection. Thus, it was shown that hcmv-miR-UL112 target major histocompatibility complex class I-related chain B (MICB). Moreover, a putative target was identified in MICA (Stern-Ginossar N, 2007 Jul. 20; 317(5836)).

MICB is a stress-induced ligand of the natural killer (NK) cell activating receptor NKG2D and is critical for the NK cell killing of virus-infected cells and tumor cells. Hcmv-miR-UL112 specifically downregulates MICB expression during viral infection, leading to decreased binding of NKG2D and reduced killing by NK cells.

Thus, we suggest using a blockmir to prevent hcmv-mir-UL112 from regulating MICB and/or MICA The target sequences are listed next. The microRNA is shown as the upper strand, the target sequence is the middle strand and a blockmir sequence is shown as the lower strand. Specific embodiments of the blockmirs will be apparent from the detailed description of the invention.

Mir-UL112 vs. MICB

```
3' UCGGACCUAGAGUGGCAGUGGA
     ||||||||||||| |||||
5' ACUCCCUGCCUGGAUCUCACCAGCACUUUCCCUCUGUUUC
   |||||||||||||||||||||||||||||||||||||||||
5' TGAGGGACGGACCTAGAGTGGTCGTGAAAGGGAGACAAAG
```

Mir-UL112 vs. MICA

```
3' UCGGACCUAGAGUGGCAGUGGA
   |||||||||||  |||||
5' AUUCCCUGCCUGGAUCUCACGAGCACUUUCCCUCUUGGUG
   ||||||||||||||||||||||||||||||||||||||||
3' TAAGGGACGGACCTAGAGTGCTCGTGAAAGGGAGAACCAC
```

Example 14

Blockmirs for Treatment or Prevention of Colorectal Cancer

Mir-21 was recently demonstrated to be a post-transcriptional regulator of tumor-suppressor Pdcd4 (Asangani I A, 2007 Oct. 29). The authors demonstrated an inverse correlation of mir-21 and Pdcd4 in 10 colorectal cell lines and demonstrated mir-21 regulation of Pdcd4 using a luciferase reporter assay. Thus, transfection of antimir-21 increased expression a luciferase-reporter containing the 3'UTR of Pdcd4 and transfection of pre-mir-21 decrease expression. Further, it was shown that mir-21 upregulates tumor cell invasion in cultured colon cancer cells and the transfection of anti-mir-21 leads to reduced intravasation and distal metastasis. Finally, it was also demonstrated that mir-21 and Pdcd4 are inversely expressed in resected patient tumors.

Since many of the effects of mir-21 are likely mediated by regulation of the tumorsupressor Pdcd4, we suggest to interfere with mir-21 regulation of Pdcd4 using a blockmir of the invention, as a means of treating or preventing cancer, more particular a means of treating or preventing intravasation and metastasis.

The microRNA is shown as the upper strand, the target sequence of Pdcd4 is the middle strand and a blockmir sequence is shown as the lower strand. Specific embodiments of the blockmirs will be apparent from the detailed description of the invention.

```
3' AGUUGUAGUCAGACUAUUCGAU
   |||  ||||||||
5' CUUCUUAAGUGGAAUAUUCUAAUAAGCUACCUUUUGUAAG
   ||||||||||||||||||||||||||||||||||||||||
   GAAGAATTCACCTTATAAGATTATTCGATGGAAAACATTC
```

Example 15

Blockmirs Targeting tnf-alfa Useful for Immunomodulation microRNA 369-3 vs. tnf

A recent report demonstrated that microRNA 369-3 is a regulator of tnf-alfa (tumor necrosis factor-alfa) expression (Vasudevan S, 2007 Nov. 29 [Epub ahead of print]). Interestingly, regulation was shown to be positive. Thus, the microRNA increased translation of tnf-alfa in serum starvation induced cell cycle arrested cells.

Tumor necrosis factor alfa is normally expressed in stimulated lymphocytes, and is critical for inflammatory responses and malignancies. Thus, various TNF-alfa antagonists are now on the market for treatment of immune related conditions such as rheumatoid arthritis and Crohns disease and second generation TNF-alfa antagonists are in development.

When circulating monocytes become adherent during the process of extravasation into inflamed tissues or in proangiogenic tumor infiltration, cell growth arrests with rapid changes in cytokine expression, including that of tnf-alfa, which further upregulates other cytokines necessary for maturation into macrophages. This response can be recapitulated in cell culture by serum starvation.

Since microRNA 369-3 is a positive regulator of tnf-expression, microRNA 369-3 inhibitors may be used as tnf-antagonists. One microRNA 369-3 inhibitor could be an antisense oligonucleotide directed to the microRNA, i.e. an antimir or antagomir.

We suggest using a blockmir to prevent microRNA 369-3 stimulation of tnf-alfa expression, e.g. when circulating monocytes adhere to inflamed tissues. Such an approach has the potential advantage that it preferentially targets activated monocytes.

The tnf-alfa 3'UTR has two anti-seed sequences of complementarity to mir-369-3 and their importance for microRNA regulation was verified by mutational analysis by Vasudevan et al.

The two antiseed sequences are indication with bold letters in the following sequence:

```
5' AUGUUUGCACUUGUGAUUAUUUAUUAUUUAUUUAUUAUUU
```

The target sequences aligned with the microRNA is shown next. The microRNA is shown as the upper strand, the target sequence is the middle strand and a blockmir sequence is shown as the lower strand. Specific embodiments of the blockmirs will be apparent from the detailed description of the invention.

```
3' UUUCUAGUUGGUACAUAAUAA
   |||||| |||||||
5' AUGUUUGCACUUGUGAUUAUUUAUUAUUUAUUUAUUAUUU
   ||||||||||||||||||||||||||||||||||||||||
3' TACAAACGTGAACACTAATAAATAATAAATAAATAATAAA

3' UUUCUAGUUGGUACAUAAUA
   ||||||| |||||||
5' UGUGAUUAUUUAUUAUUUAUUUAUUAUUUAUUUAUUUACA
   ||||||||||||||||||||||||||||||||||||||||
3' ACACTAATAAATAATAAATAAATAATAAATAAATAAATGT
```

Importantly, the same blockmir may be used to block both target sites.

Mir-155 vs. tnf

Another recent publication found that LPS stimulation of macrophages resulted in upregulation of mir-155 and downregulation of mir-125b and demonstrated tnf-regulation by mir-155 and mir-125b (Tili E, 2007 Oct. 15; 179(8)). Interestingly, regulation by mir-155 was positive. Thus, blockmirs preventing mir-155 from regulating tnf may be used similarly to blockmirs preventing mir-369.3 regulation. The authors did not report any target sequences of mir-155 in the 3'UTR of the tnf alfa mRNA. However, sequence analysis using RNA-hybrid identifies the following very good target sites (the microRNA is shown in as the upper strand, the target sequence as the middle sequence and a blockmir sequence is shown as the lower strand):

```
    3' ACAAUUACGAUUAUACAUCCUC
           ||||   |||  ||||||
    5' UUUACAGAUGAAUGUAUUUAUUUGGGAGACCGGGGUAUCC
       ||||||||||||||||||||||||||||||||||||||||
    3' AAATGTCTACTTACATAAATAAACCCTCTGGCCCCATAGG

3' ACAAUUACGAUUAUACAUCCUC
                       ||||||||
    5' GGGUAUCCUGGGGGACCCAAUGUAGGAGCUGCCUUUUUUC
       ||||||||||||||||||||||||||||||||||||||||
    3' CCCATAGGACCCCTGGGTTACATCCTCGACGGAAAAAAG
```

Mir-125b vs tnf

Mir-125b was demonstrated to be a negative regulator of tnf-alfa expression when macrophages are stimulated with LPS. Negative regulation of tnf-alfa may be of interest e.g. for patients receiving treatment with a tnf-alfa antagonist. It is well known that such treatment poses risk of activating a latent tuberculosis infection and increased susceptibility for infections in general. Preventing mir-125b regulation of tnf-alfa may allow macrophage activation, thus enabling immune defense against infections, even when the patient is treated with a tnf-alfa antagonist. It is of note that most tnf-alfa antagonists are extracellular (antibodies or soluble receptors) and thus, tnf-alfa may be decreased extracellularly using a tnf-alfa antagonist and increased intracellularly using a blockmir preventing mir-125b regulation of tnf-alfa expression. Furthermore, there may be conditions where mir-125b regulation of tnf-alfa expression is indeed positive. Thus, some microRNAs were reported to be repressors in proliferating cells and activators in cell cycle arrested cells, as described above. Therefore, a blockmir preventing mir-125b regulation may also be used for decreasing tnf-alfa expression.

Sequence analysis using RNA-hybrid identifies a number of target sites. The microRNA is shown in as the upper strand, the target sequence as the middle sequence and a blockmir sequence is shown as the lower strand. Specific embodiments of the blockmir will be apparent from the description of the invention.

a)
```
         3'       AGUGUUCAAUCCCAGAGUCCCU
                  ||||||  |||||||
    5' GCUCAAAAAGAGAAUUGGGGGCUUAGGGUCGGAACCCAAG
       ||||||||||||||||||||||||||||||||||||||||
    3' CGAGTTTTTCTCTTAACCCCGAATCCCAGCCTTGGGTTC
```
b)
```
         3'       AGUGUUCAAUCCCAGAGUCCCU
                     ||  |||||||
    5' CUAGAAAUUGACACAAGUGGACCUUAGGCCUUCCUCUCUC
       ||||||||||||||||||||||||||||||||||||||||
    3' GATCTTTAACTGTGTTCACCTGGAATCCGGAAGGAGAGAG
```
c)
```
         3'       AGUGUUCAAUCCCAGAGUCCCU
                                |||||||
    5' CUGACAUCUGGAAUCUGGAGACCAGGGAGCCUUUGGUUCU
       ||||||||||||||||||||||||||||||||||||||||
    3' GACTGTAGACCTTAGACCTCTGGTCCCTCGGAAACCAAGA
```
d)
```
         3'       AGUGUUCAAUCCCAGAGUCCCU
                                ||||||
    5' CAUUGCUGAGCCUCUGCUCCCCAGGGGAGUUGUGUCUGUA
       ||||||||||||||||||||||||||||||||||||||||
    3' GTAACGACTCGGAGACGAGGGGTCCCCTCAACACAGACAT
```

Mir-125b-1* (processed from the same pre-mir as mir-125b) also have target sites in the tnf-UTR:

a)
```
         3'       UCGAGGGUUCUCGGAUUGGGCA
                   ||  ||||||||
    5' AACCUGGGGAUUCAGGAAUGUGUGGCCUGCACAGUGAAGUG
       |||||||||||||||||||||||||||||||||||||||||
    3' TTGGACCCTAAGTCCTTACACACCGGACGTGTCACTTCAC
```
b)
```
         3'       UCGAGGGUUCUCGGAUUGGGCA
                           |||||||
    5' AGGCUGUUCCCAUGUAGCCCCCUGGCCUCUGUGCCUUCUU
       ||||||||||||||||||||||||||||||||||||||||
    3' TCCGACAAGGGTACATCGGGGACCGGAGACACGGAAGAA
```

Example 16

Blockmirs Targeting Tumor Suppressors SuFu and Fus-1

MicroRNA-378 was recently demonstrated to promote cell survival, tumor growth and angiogenesis by targeting the two tumor suppressors, SuFu and Fus-1 expression (Lee D Y, 2007 Dec. 18, Epub 2007 Dec. 11). Among others, the microRNA binding site was confirmed by mutational analysis. Blockmirs preventing microRNA-378 regulation may be useful for treatment or prevention of cancer.

Mir-378 vs. sufu

As in the previous examples, the microRNA is shown in as the upper strand, the target sequence as the middle sequence and a blockmir sequence is shown as the lower strand. Specific embodiments of the blockmir will be apparent from the description of the invention.

```
         3'       UGUGUCCUGGACCUCAGUCCUC
                             ||||||||
    5' UGCCUGGGUCCCUGUUACAAGUCAGGAGCCCUGUAGGGAG
       ||||||||||||||||||||||||||||||||||||||||
    3' ACGGACCCAGGGACAATGTTCAGTCCTCGGGACATCCCTC
```

Mir-378 vs. fus-1 a)
```
         3'       UGUGUCCUGGACCUCAGUCCUC
                            |||||||
    5' AGCACAGCAGGGCAUAUACCAGUCAGGAAUGCCCGUUACC
       ||||||||||||||||||||||||||||||||||||||||
    3' CAACTCTCTCACGTCCGACCCCAGTCCTGTCCGACGCCTA
``` b) Another potential target site is:

```
         3'       UGUGUCCUGGACCUCAGUCCUC
                           |||||||||
    5' GUUGAGAGAGUGCAGGCUGGGGUCAGGACAGGCUGCGGAU
       ||||||||||||||||||||||||||||||||||||||||
    3' CAACTCTCTCACGTCCGACCCCAGTCCTGTCCGACGCCTA
```

Example 17

Blockmirs for Prevention of Tumour Invasion and Metastasis

MicroRNAs mir-373 and mir-520c has been shown to promote tumour invasion and metastasis (Huang Q, 2008 February; Epub 2008 Jan. 13.) The authors demonstrated that the migration phenotype of cells mir-373 and mir-520c can be explained by downregulation of CD44. Reduced expression of CD44, which encodes a cell surface receptor for hyaluronan, has previously been reported to cause enhanced tumor progression in line with a role in migration. Evidence for two microRNA binding site in the 3'UTR was also given in the paper and it was shown that deletion of two microRNA binding sites near about 70 and 140 nt. from the 3'end of the UTR abolished regulation. The authors speculate that other targets of the two microRNAs may be involved in the migration phenotype. However, they also demonstrate that siRNA knock-out of CD44 also has a migration phenotype supporting the importance of CD44 downregulation for migration and invasion.

We suggest to block CD44 downregulation using blockmirs. The two preferred target sites are those close to the 3'end of the UTR (position 3001 and position 2927):

Mir-373 vs. CD44

One potential target site for mir-373 was identified near the 3'end of the UTR.

Complex from RNA hybrid:

```
position 3001
target 5'    U  UG              A          A    3'
             AU CU  GAGUUGAA GCACUU
             UG GG  UUUAGCUU CGUGAA
miRNA  3'       UG  GU                  G    5'
```

The complex shown as in the previous examples; the microRNA is shown in as the upper strand, the target sequence as the middle sequence and a blockmir sequence is shown as the lower strand. Specific embodiments of the blockmir will be apparent from the description of the invention.

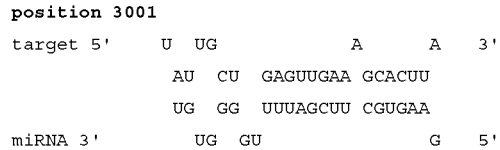

Mir-520c vs. CD44

Three potential target sites for mir-520c were identified:

First is shown the complex from RNA hybrid. Then the complex is shown as in the previous examples.

a)
```
position 2083
target 5' C    UG  UUCCAC              U  3'
          CAGAGA GUU  UCCUUCUAGA
          GUCUUU CGA  AGGGAGAUCU
miRNA  3'    CA                    C  5'
```

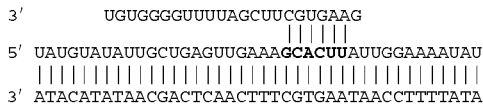

b)
```
position 485
target 5' A     CC              A  3'
          CAGA       CCCUCUAGA
          GUCU       GGGAGAUCU
miRNA  3'    UUCACGAA         C  5'
```

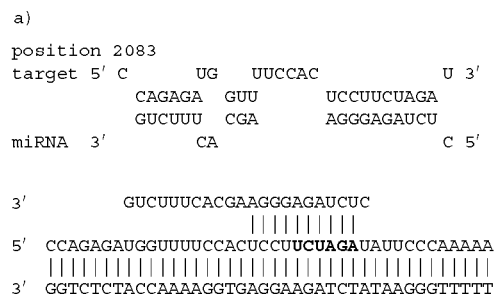

c)
```
position 2927
target 5' U    CACACCC         U  3'
          CAGAG      UUCCUCUGG
          GUCUU      AGGGAGAUC
miRNA  3'    UCACGA         UC  5'
```

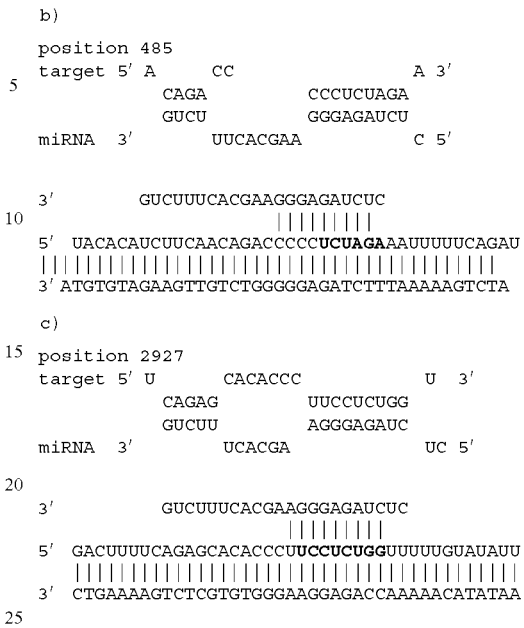

Example 18

Blockmir Targeting PTEN for Treatment of Cancer

Mir-214 has been to induce cell survival and cisplatin resistance through targeting the 3'UTR of PTEN, which leads to down-regulation of PTEN and activation of the Akt pathway (Yang H, 2008 Jan.). A mir-214 binding site in the 3'UTR of PTEN was demonstrated. The microRNA binding site was verified using mutational analysis and reporter systems. Moreover, it was shown that bypassing microRNA regulation of PTEN with PTEN cDNA lacking the 3'UTR reduces cell survival as does also introduction of an Akt inhibitor. Thus, a blockmir may be used to prevent microRNA regulation of PTEN, which in turn will prevent activation of the Akt pathway. Such a blockmir may be co-administered with cisplatin or other chemotherapy drugs to prevent the generation of resistance. An antimir directed to the mir-214 may also be used, but in that case chances of side effects may be increased.

The following complex may be formed between mir-214 and the target site identified in the above work:

a)
```
position 993
target 5' U    A      UCAA    AUAAUA         G  3'
             ACU  GUUU     UC         CCUGCUGU
             UGA  CGGA     AG         GGACGACA
miRNA  3'         C          ACAC              5'
```

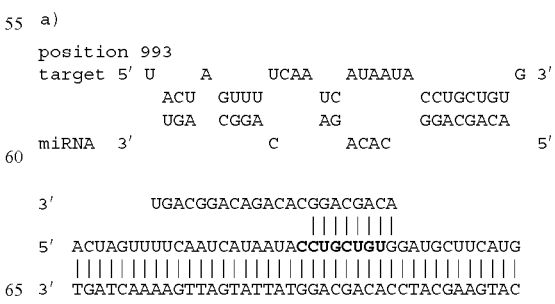

Other binding sites are shown in the following complexes:

```
b)

position 629
target 5'     G    GC     AC               U 3'
              GCC  UGUC   UGCUUGUUGU
              CGG  ACAG   ACGGACGACA
miRNA  3' UGA         AC              5'

3'       UGACGGACAGACACGGACGACA
                ||||||||||
5' GGAAUUGGCCGCUGUCACUGCUUGUUGUUUGCGCAUUUUU
   ||||||||||||||||||||||||||||||||||||||||
3' CCTTAACCGGCGACAGTGACGAACAACAAACGCGTAAAAA c)

position 3196
target 5'  A     UCAUCCCAAUCAGA      CAUUUGUUAU        A  3'
           UGCC                UGUC             UGUGUUUGUU
           ACGG                ACAG             ACACGGACGA
miRNA 3' UG                                              CA 5'

3'        UGACGGACAGACACGGACGACA
                  ||||||||||
5' AGAUGUCCAUUUGUUAUUGUGUUUGUUAACAACCCUUUAU
   ||||||||||||||||||||||||||||||||||||||||
3' TCTACAGGTAAACAATAACACAAACAATTGTTGGGAAATA
```

Example 19

Blockmirs for Treatment of Cancer

MicroRNA-27a was recently demonstrated to be a repressor of ZBTB10, which is a negative regulator of Sp1, Sp3 and Sp4 (Mertens-Talcott SU, 2007 November). Thus, transfection of ER-negative MDA-MB-231 breast cancer cells with antisense miR-27a resulted in increased expression of ZBTB10 mRNA and decreased expression of Sp1, Sp3 and Sp4. In addition, antisense mir-27a transfection were accompanied by decreased expression of Sp-dependent survival and angiogenic genes, including surviving, vascular endothelial growth factor (VEGF) and VEGF receptor 1 (VEGFR1). Similar results were obtained with transfection of ZBTB10 expression plasmid. Thus, an antisense molecule directed to mir-27a may be used to treat cancer. We suggest blocking mir-27a suppression of ZBTB10 using a blockmir directed to ZBTB10.

Mir-27a vs ZBTN10 3'UTR:

```
position 96
target 5' U    U   UAG       AUGUU           A  3'
          GC GGA    UAGUU         GCUGUGAA
          CG CCU    AUCGG         UGACACUU
miRNA  3'         UGA                        5'

3'          CGCCUUGAAUCGGUGACACUU
                  |||||||||||
5' GCUGGAUAGUAGUUAUGUUGCUGUGAAAACUGUAGGGUCA
   |||||||||||||||||||||||||||||||||||||||||
3' CGACCTATCATCAATACAACGACACTTTTGACATCCCAGT
```

As in the previous examples, the upper sequence is the microRNA, the middle sequence is the target sequence and the lower strand is an exemplary blockmir which can be truncated at both ends. Specific embodiments will be apparent from the detailed description.

Mi-27a vs. Myt-1

Mir-27a was also demonstrated to regulate Myt-1 further contributing to the oncogenic activity of the microRNA. Myt-1 blocks cell cycle progression at $G_2$-M. Therefore a blockmir that prevents mir-27a of Myt-1 is also of interest.

Sequence analysis identifies two putative target sites and corresponding complexes between the microRNA and the 3'UTR of Myt-1 a)
```
position 2620
target 5' U         CACA              U 3'
          GUGGAAU       AGUUGCUGUGA
          CGCCUUG       UCGGUGACACU
miRNA 3'         AA                U 5'

3'       CGCCUUGAAUCGGUGACACUU
              |||||||||||
5' AAUGUGUGGAAUCACAAGUUGCUGUGAUACUUCAUUUUUA
   ||||||||||||||||||||||||||||||||||||||||
3' TTACACACCTTAGTGTTCAACGACACTATGAAGTAAAAAT
``` b)
```
position 2414
target 5' U   U   C   UUCAUA    A              U 3'
          GC GA  CU          UGG  UUAUUGUGAG
          CG CU  GA          AUC  GGUGACACUU
miRNA  3'      C    U                           5'

3'          CGCCUUGAAUCGGUGACACUU
                  |||||||||||
5' CUGACCUUUCAUAUGGAUUAUUGUGAGUCAUCAGAGUUUA
   ||||||||||||||||||||||||||||||||||||||||
3' GACTGGAAAGTATACCTAATAACACTCAGTAGTCTCAAAT
```

References

Asangani I A, R. S. (2007 Oct. 29). MicroRNA-21 (miR-21) post-transcriptionally downregulates tumor suppressor Pdcd4 and stimulates invasion, intravasation and metastasis in colorectal cancer. *Oncogene*.

Galardi S, M. N. (2007). miR-221 and miR-222 expression affects the proliferation potential of human prostate carcinoma cell lines by targeting p27Kip1. *J Biol Chem*, August 10; 282(32):23716-24.

Gillies J K, L. I. (2007). Regulation of p27Kip1 by miRNA 221/222 in glioblastoma. *Cell Cycle*, June; 6(16):2005-9.

Gupta A, G. J. (2006). Anti-apoptotic function of a microRNA encoded by the HSV-1 latency-associated transcript. *Nature*, July 6; 442(7098):82-5.

Huang J, W. F. (2007 October; 13(10),Epub 2007 Sep. 30). Cellular microRNAs contribute to HIV-1 latency in resting primary CD4(+) T lymphocytes. *Nat Med.*, 1241-7.

Huang Q, G. K.-S. (2008 February; Epub 2008 Jan 13). The microRNAs miR-373 and miR-520c promote tumour invasion and metastasis. *Nat Cell Biol.*, 10(2):202-10.

Jopling C L, Y. M. (2005). Modulation of hepatitis C virus RNA abundance by a liver-specific MicroRNA. *Science*, September 2; 309(5740):1577-81.

Ie Sage C, N. R. (2007). Regulation of the p27(Kip1) tumor suppressor by miR-221 and miR-222 promotes cancer cell proliferation. *EMBO J.*, August 8; 26(15):3699-708. Epub 2007 Jul. 12.

Lee D Y, D. Z. (2007 Dec. 18, Epub 2007 Dec. 11). MicroRNA-378 promotes cell survival, tumor growth, and angiogenesis by targeting SuFu and Fus-1 expression. *Proc Natl Acad Sci USA*, 104(51):20350-5.

Ma L, T.-F. J. (2007 Oct. 11; 449(7163), Epub 2007 Sep. 26). Tumour invasion and metastasis initiated by microRNA-10b in breast cancer. *Nature*, 682-8.

Meng F, H. R.-J. (2007). MicroRNA-21 regulates expression of the PTEN tumor suppressor gene in human hepatocellular cancer. *Gastroenterology, August;* 133(2):647-58. Epub 2007 May 21.

Mertens-Talcott S U, C. S. (2007 November). The oncogenic microRNA-27a targets genes that regulate specificity protein transcription factors and the G2-M checkpoint in MDA-MB-231 breast cancer cells. *Cancer Res*, 15; 67(22): 11001-11.

Poy M N, E. L. (2004). A pancreatic islet-specific microRNA regulates insulin secretion. *Nature*, November 11; 432(7014), 226-30.

Sonkoly E, W. T.-L. (2007, Jul. 11). MicroRNAs: novel regulators involved in the pathogenesis of Psoriasis? *PLoS ONE*, 2(7):e610.

Stern-Ginossar N, E. N.-W. (2007 Jul. 20; 317(5836)). Host immune system gene targeting by a viral miRNA. *Science*, 376-81.

Taganov K D, B. M. (2006). NF-kappaB dependent induction of microRNA miR-146, an inhibitor targeted to signaling proteins of innate immune responses. *Proc Natl Acad Sci USA*, 103: 12481-12486.

Tili E, M. J. (2007 Oct. 15; 179(8)). Modulation of miR-155 and miR-125b levels following lipopolysaccharide/TNF-alpha stimulation and their possible roles in regulating the response to endotoxin shock. *J Immunol*, 5082-9.

Vasudevan S, T. Y. (2007 Nov. 29 [Epub ahead of print]). Switching from Repression to Activation: MicroRNAs Can Up-Regulate Translation. *Science*.

Volinia S, C. G. (2006). A microRNA expression signature of human solid tumors defines cancer gene targets. *Proc Natl Acad Sci USA, February* 14; 103(7):2257-61.

Volinia S, C. G. (2006 Feb. 14; 103(7)). A microRNA expression signature of human solid tumors defines cancer gene targets. *Proc Natl Acad Sci USA*, 2257-61.

Voorhoeve P M, I. S. (2006). A genetic screen implicates miRNA-372 and miRNA-373 as oncogenes in testicular germ cell tumors. *Cell, March* 24; 124(6):1169-81.

Xiao C, C. D. (2007 Oct. 5; 131(1)). MiR-150 Controls B Cell Differentiation by Targeting the Transcription Factor c-Myb. *Cell*, 146-59.

Yang H, K. W. (2008 Jan). MicroRNA expression profiling in human ovarian cancer: miR-214 induces cell survival and cisplatin resistance by targeting PTEN. *Cancer Res*, 15; 68(2):425-33.

Zhu S, S. M. (2007). MicroRNA-21 targets the tumor suppressor gene tropomyosin 1 (TPM1). *J Biol Chem.* 2007 May 11; 282(19):14328-36., May 11; 282(19):14328-36.

---

The invention claimed is:

1. A method for blocking microRNA-122 activity in a target cell, the method comprising introducing to the target cell a blockmir comprising a contiguous sequence which is complementary to at least 8 contiguous bases of SEQ ID NO: 3,
wherein the blockmir comprises at least one non-natural nucleotide such that it does not activate any RNase H and does not recruit any RNAi machinery.

2. The method of claim 1, wherein the blockmir forms base pairing with at least residues 22-27 of SEQ ID NO:3.

3. The method of claim 1, wherein the target cell is infected with Hepatitis C Virus (HCV) RNA.

4. The method of claim 3, wherein introducing the blockmir to the target cell reduces the amount of HCV RNA in the target cell.

5. The method of claim 4, wherein the amount of HCV RNA in the target cell is reduced by about 80%.

6. The method of claim 1, wherein the blockmir further comprises locked nucleic acid (LNA) units.

7. The method of claim 1, wherein the blockmir is capable of forming base pairs with at least 8 contiguous bases according to SEQ ID NO:3, and wherein the base pairs are consecutive over a length selected from the group consisting of at least 9 bases, at least 10 bases, at least 11 bases, at least 12 bases, at least 13 bases, at least 14 bases, at least 15 bases, at least 16 bases, at least 17 bases, at least 18 bases, at least 19 bases, at least 20 bases, at least 22 bases, at least 25 bases, at least 30 bases, and at least 35 bases.

8. The method of claim 1, wherein the blockmir is capable of forming base pairs with at least 8 contiguous bases according to SEQ ID NO:3, and wherein the base pairs are consecutive over a length selected from the group consisting of at least 9 bases, at least 10 bases, at least 11 bases, at least 12 bases, at least 13 bases, at least 14 bases, at least 15 bases, and at least 16 bases.

9. The method of claim 1, wherein the blockmir is capable of forming base pairs with at least 8 contiguous bases according to SEQ ID NO:3, and wherein the base pairs are consecutive over a length selected from the group consisting of at least 17 bases, at least 18 bases, at least 19 bases, at least 20 bases, at least 22 bases, at least 25 bases, at least 30 bases, and at least 35 bases.

10. The method of claim 1, wherein the base pairs extend to residue 28 of SEQ ID NO:3.

11. The method of claim 1, wherein the base pairs begin at residue 7 of SEQ ID NO:3.

12. The method of claim 1, wherein the method is performed in vivo.

13. The method of claim 1, wherein the method is performed ex vivo.

14. The method of claim 1, wherein the method is performed in vitro.

* * * * *